(12) United States Patent
Biris et al.

(10) Patent No.: US 10,390,927 B2
(45) Date of Patent: Aug. 27, 2019

(54) GRAFT SCAFFOLD WITH PLASMONIC ACTIVITY, AND METHODS OF MAKING AND USING SAME

(71) Applicant: BOARD OF TRUSTEES OF THE UNIVERSITY OF ARKANSAS, Little Rock, AR (US)

(72) Inventors: Alexandru S. Biris, Little Rock, AR (US); Karrer Alghazali, Little Rock, AR (US); Zeid A. Nima, Little Rock, AR (US)

(73) Assignee: BOARD OF TRUSTEES OF THE UNIVERISTY OF ARKANSAS, Little Rock, AR (US)

( * ) Notice: Subject to any disclaimer, the term of this patent is extended or adjusted under 35 U.S.C. 154(b) by 291 days.

(21) Appl. No.: 15/487,614

(22) Filed: Apr. 14, 2017

(65) Prior Publication Data

US 2017/0296321 A1    Oct. 19, 2017

Related U.S. Application Data

(60) Provisional application No. 62/322,466, filed on Apr. 14, 2016.

(51) Int. Cl.
*A61F 2/02*        (2006.01)
*A61L 27/54*       (2006.01)
(Continued)

(52) U.S. Cl.
CPC ............ *A61F 2/02* (2013.01); *A61B 17/1128* (2013.01); *A61L 27/20* (2013.01); *A61L 27/54* (2013.01); *A61B 2017/00526* (2013.01); *A61B 2017/00893* (2013.01); *A61F 2/0063* (2013.01); *A61F 2002/0086* (2013.01);
(Continued)

(58) Field of Classification Search
CPC ............... A61F 2/02; A61F 2210/0004; A61F 2210/0076; A61F 2/0063; A61F 2002/0086; A61F 2002/2835; A61F 2250/0067; A61L 27/54; A61L 27/20; A61L 2300/102; A61L 2430/02; A61L 2300/414; A61L 2430/34; A61L 2400/12; A61L 2300/252; A61B 17/1128; A61B 2017/00526; A61B 2017/00893
See application file for complete search history.

(56) References Cited

U.S. PATENT DOCUMENTS

2009/0035446 A1    2/2009  Kwon
2014/0358116 A1   12/2014  Ghandehari et al.
2015/0039097 A1    2/2015  Biris et al.

FOREIGN PATENT DOCUMENTS

WO       2016046847 A1    3/2016

OTHER PUBLICATIONS

Alghazali, K. M., et al., 2015. Bone-tissue engineering: complex tunable structural and biological responses to injury, drug delivery, and cell-based therapies. Drug Metabolism Reviews, 47, 431-454.
(Continued)

*Primary Examiner* — Trevor Love
(74) *Attorney, Agent, or Firm* — Locke Lord LLP; Tim Tingkang Xia, Esq.

(57) ABSTRACT

A two dimensional (2D) active plasmonic scaffold includes a polymer film and one or more nanoparticle layers disposed on the polymer film. The nanoparticles has functional groups attached thereon. A three dimensional (3D) structure fabricated using the 2D scaffold.

19 Claims, 16 Drawing Sheets

(51) Int. Cl.
   A61L 27/20    (2006.01)
   A61B 17/11    (2006.01)
   A61F 2/00     (2006.01)
   A61B 17/00    (2006.01)
   A61F 2/28     (2006.01)

(52) U.S. Cl.
   CPC .......... A61F 2002/2835 (2013.01); A61F 2210/0004 (2013.01); A61F 2210/0076 (2013.01); A61F 2250/0067 (2013.01); A61L 2300/102 (2013.01); A61L 2300/252 (2013.01); A61L 2300/414 (2013.01); A61L 2400/12 (2013.01); A61L 2430/02 (2013.01); A61L 2430/32 (2013.01); A61L 2430/34 (2013.01)

(56) References Cited

OTHER PUBLICATIONS

Barros, C. S., et al., 2011. Extracellular matrix: functions in the nervous system. Cold Spring Hart Perspect Biol, 3, a005108.

Bayer, I. S., et al., 2013. Fabrication of bionanocomposites comprising flat nanocrystals of calcium in collagen fibers exhibiting hardness comparable to metal. RSC Advances, 3, 20315-20323.

Birch, R., et al., 2000. Surgical disorders of the peripheral nerves. Acta Orthop Scand, 71(2), 217-221.

Castro, C., et al., 2005. Two-month ciprofloxacin implants for multibacterial bone infections. European Journal of Pharmaceutics and Biopharmaceutics, 60, 401-406.

De Ruiter, G. C. W., et al., 2009. Designing ideal conduits for peripheral nerve repair. Neurosurgical focus, 26, E5-E5.

Gnavi, S., et al., 2015. The Effect of Electrospun Gelatin Fibers Alignment on Schwann Cell and Axon Behavior and Organization in the Perspective of Artificial Nerve Design. International Journal of Molecular Sciences, 16, 12925-12942.

Henley, J. et al., 2004. Guiding Neuronal Growth Cones by Ca(2+) Signals: During axon pathfinding in the developing nervous system, spatiotemporal patterns of Ca(2+) signals can govern growth cone extension and steering—by symmetric versus asymmetric regulation of cytoskeletal and membrane dynamics. Trends in cell biology, 14, 320-330.

Hsu, S. H., et al., 2013. New nerve regeneration strategy combining laminin-coated chitosan conduits and stem cell therapy. Acta Biomater, 9, 6606-15.

Keating, J. F. et al., 2001. Substitutes for autologous bone graft in orthopaedic trauma. The Journal of bone and joint surgery. British volume, 83, 3-8.

Li, Z., et al., 2005. Chitosan-alginate hybrid scaffolds for bone tissue engineering. Biomaterials, 26, 3919-3928.

Nikoobakht, B. et al., 2003. Preparation and Growth Mechanism of Gold Nanorods (NRs) Using Seed-Mediated Growth Method. Chemistry of Materials, 15, 1957-1962.

Orza, A. I., et al., 2014. Multistructural biomimetic substrates for controlled cellular differentiation. Nanotechnology, 25, 1-13.

Paviolo, C., et al., 2014. Laser exposure of gold nanorods can induce intracellular calcium transients. J Biophotonics, 7, 761-5.

Ramburrun, P., et al., 2014. A Review of Bioactive Release from Nerve Conduits as a Neurotherapeutic Strategy for Neuronal Growth in Peripheral Nerve Injury. BioMed Research International, 2014, 19.

Rousseau, M., et al., 2014. In vivo assessment of a multicomponent and nanostructural polymeric matrix as a delivery system for antimicrobials and bone morphogenetic protein-2 in a unicortical tibial defect in goats. American Journal of Veterinary Research, 75, 240-250.

Schmidt, C. E. et al., 2003. Neural Tissue Engineering: Strategies for Repair and Regeneration. Annual Review of Biomedical Engineering, 5, 293-347.

Vella, F. 1994. Molecular biology of the cell (third edition): by B Alberts, D Bray, J Lewis, M Raff, K Roberts and J D Watson. pp. 1361. Garland Publishing, New York and London. 1994. Biochemical Education, 22, 164-164.

Vögelin, E., et al., 2005. Healing of a Critical-Sized Defect in the Rat Femur with Use of a Vascularized Periosteal Flap, a Biodegradable Matrix, and Bone Morphogenetic Protein. The Journal of Bone & Joint Surgery, 87, 1323-1331.

Brown, et al., "Gold Nanoparticles for the Improved Anticancer Drug Delivery of the Active Component of Oxaliplatin", JACS Artiles, 2010, pp. 4678-4684, vol. 132.

Korean Intellectual Property Office, "International Search Report for PCT/US2017/027604", KR, dated Aug. 18, 2017.

400

US 10,390,927 B2

GRAFT SCAFFOLD WITH PLASMONIC ACTIVITY, AND METHODS OF MAKING AND USING SAME

CROSS-REFERENCE TO RELATED PATENT APPLICATION

This application claims priority to and the benefit of, pursuant to 35 U.S.C. § 119(e), U.S. provisional patent application Ser. No. 62/322,466, filed Apr. 14, 2016, which is incorporated herein in its entirety by reference.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under grant number IIA-1457888 awarded by the National Science Foundation. The government has certain rights in the invention.

FIELD

The invention relates generally to tissue graft, and more particularly to two dimensional (2D) and three dimensional (3D) structure scaffolds with plasmonic activity, method of making the same, and applications of the same.

BACKGROUND

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

A treatment of complex tissue injury or wound requires significant and potent techniques and tools to achieve rapid healing and guarantee a full recovery of the damaged zone. A traditional surgical treatment for such a severe damage is through tissue grafts. Three kinds of tissue grafts were reported, the first type called autograft which is obtained from the patient's body, the second type known as allograft is based on using a cadaver of the same species while the third one is xenograft based on a cadaver of a different species. Among these three techniques autograft is the preferred treatment, and it has been reported as such for many years. However, these procedures are associated with many shortcomings. For instance, harvesting the required tissue is a complicated and painful process for both the patient and the surgeon, and it requires a long recovery timeframe for the patient. In addition, it requires two surgical procedures which lead to an extended hospitalization period, and thus increases the treatment cost. Whereas in the other type of tissue graft, allograft and xenograft, the main stumbling shortcoming is the potential rejection of the implant by the body in addition to the possibility of infection, and transmission of diseases.

Therefore, a heretofore unaddressed need exists in the art to address the aforementioned deficiencies and inadequacies.

SUMMARY

In one aspect, the present inventions relates to a two dimensional (2D) active plasmonic scaffold. In certain embodiments, the 2D active plasmonic scaffold includes a polymer film and a first nanoparticle layer. The polymer film has a first surface. The first nanoparticle layer has first nanoparticles. The first nanoparticles are partially embedded on the first surface of the polymer film. The first nanoparticles comprising first functional groups attached thereon.

In certain embodiments, the 2D active plasmonic scaffold further includes a second nanoparticle layer having second nanoparticles disposed on the first nanoparticles. The second nanoparticles includes second functional groups attached thereon, and the second functional groups are different from the first functional groups.

In certain embodiments, the polymer film is made from chitosan.

In certain embodiments, the first functional groups are one of —COOH and —NH$_2$, the second functional groups are the other one of —COOH and —NH$_2$, and the first functional groups and the second functional groups are bonded.

In certain embodiments, the 2D active plasmonic scaffold further includes active molecules attached to at least one of the first functional groups and the second functional groups, and the active molecules comprises at least one of extracellular proteins and drugs.

In certain embodiments, the 2D active plasmonic scaffold further comprising active molecules attached to the first functional groups, and the active molecules comprises at least one of extracellular proteins and drugs.

In another aspect, the present invention relates to a three dimensional (3D) active plasmonic scaffold made from the 2D active plasmonic scaffold. In certain embodiments, the 3D active plasmonic scaffold includes a tubular member and a plurality of strip members stacked together and disposed inside the tubular member. Each of the tubular member and the plurality of strip members are made of the 2D active plasmonic scaffold as described above. Sizes of the strips match an inner space of the tubular member.

In certain embodiments, the tubular member is formed by rolling the 2D active plasmonic scaffold, and the first surface of the 2D active plasmonic scaffold faces inside of the tubular member.

In certain embodiments, the tubular member and the strip members are stick together through welding using acetic acid and stabilizing using sodium hydroxide.

In a further aspect, the present invention relates to a method for making a two dimensional (2D) active plasmonic scaffold. In certain embodiments, the method includes providing a first polymer film and first nanoparticles, and embedding the first nanoparticles on a first surface of the first polymer film to form a first nanoparticle layer. The first nanoparticles has first functional groups attached thereon.

In certain embodiments, the first polymer film is provided by: dissolving 2 mg chitosan in 100 ml of 1% acetic acid, and stirring for 24 hours to obtain a uniform polymer solution; and casting the uniform polymer solution in a glass mold and drying inside a furnace for 24 hours at 50° C. to obtain the first polymer film.

In certain embodiments, the first nanoparticles are gold nanorods with functional groups (AuNR—X). The AuNR—X are provided by: mixing 5 ml of 0.2 M cetyl trimethyl ammonium bromide (CTAB) solution with 5 ml 0.0005 M chloroauric acid ($HAuCl_4$) solution, and then adding 600 ml of 0.01 M sodium borohydrid ($NaBH_4$) solution and mixing to form a seed solution; mixing 5 ml of 0.2 M CTAB solution with 150 ml of 0.004 M silver nitrate solution, and then adding 5 ml of 0.001 M $HauCl_4$ and mixing to form a first mixture; adding 70 ml of 0.0788 M ascorbic acid to the first mixture to form a second mixture; adding 12 ml of the seed solution to the second mixture to form a third mixture; maintaining the third mixture at 30° C. for 40 minutes; centrifuging the third mixture at 10,000 rpm for 30 minutes to obtain the gold nanorods (AuNRs); dispersing the AuNRs in 2 ml of thiolated polyethylene glycol with functional groups (HS-PEG-$NH_2$ or HS-PEG-COOH) and stirring for 15 minutes; adding 1.8 ml of thiolated polyethylene glycol (HS-PEG) stabilizer and stirring at room temperature overnight; centrifuging at 10,000 rpm for 20 minutes; and washing and re-suspending in 1X phosphate buffered saline (PBS) to form the AuNR—X.

In certain embodiments, the step of embedding includes: applying 1% acetic acid onto the first surface of the first polymer film; adding 2 mg/ml of the AuNR—X in an aqueous solution to the first surface of the first polymer film; shaking the first polymer film with the added 1% acetic acid and the AuNR—X; and keeping the mold inside a furnace for 24 hours at 50° C. to obtain the 2D active plasmonic scaffold.

In certain embodiments, the method further includes: adding second nanoparticles onto the embedded first nanoparticles to form a second nanoparticle layer. The second nanoparticles have second functional groups attached thereon, and the second functional groups are different from the first functional groups.

In certain embodiments, the first functional groups are one of —COOH and —$NH_2$, and the second functional groups are the other one of —COOH and —$NH_2$.

In certain embodiments, the method further includes: adding active molecules onto the second nanoparticles, wherein the active molecules interact with the second functional groups. In certain embodiments, the active molecules include at least one of extracellular proteins and drugs.

In certain embodiments, the method further includes: adding active molecules onto the first nanoparticles, wherein the active molecules interact with the first functional groups. In certain embodiments, the active molecules include at least one of extracellular proteins and drugs.

In yet another aspect, the present invention relates to a method for making a three dimensional (3D) active plasmonic scaffold from 2D attive plasmonic scaffold. In certain embodiments, the method includes: rolling a first active plasmonic scaffold to form a conduit; cutting a second active plasmonic scaffold to form strips; filling the conduit with the strips; applying a bonding solution over the conduit and the strips to stick the conduit and the strips to each other; immersing the conduit and the strips in a stabilizing solution to stabilize the conduit and the strips; and washing the conduit and the strips to obtain the 3D active plasmonic scaffold.

In certain embodiments, each of the first active plasmonic scaffold and the second active plasmonic scaffold comprises a polymer layer and a nanoparticle layer partially embedded on one side of the polymer layer.

In certain embodiments, the nanoparticle layer comprises gold nanorods with functional groups (AuNR—X) of —$NH_2$ or —COOH.

In certain embodiments, the binding solution 1% acetic acid, and the stabilizing solution is sodium hydroxide.

These and other aspects of the present invention will become apparent from the following description of the preferred embodiment taken in conjunction with the following drawings, although variations and modifications therein may be effected without departing from the spirit and scope of the novel concepts of the invention.

BRIEF DESCRIPTION OF THE DRAWINGS

The accompanying drawings illustrate one or more embodiments of the disclosure and, together with the written description, serve to explain the principles of the disclosure. The same reference numbers may be used throughout the drawings to refer to the same or like elements in the embodiments.

DETAILED DESCRIPTION

Figure 1A:
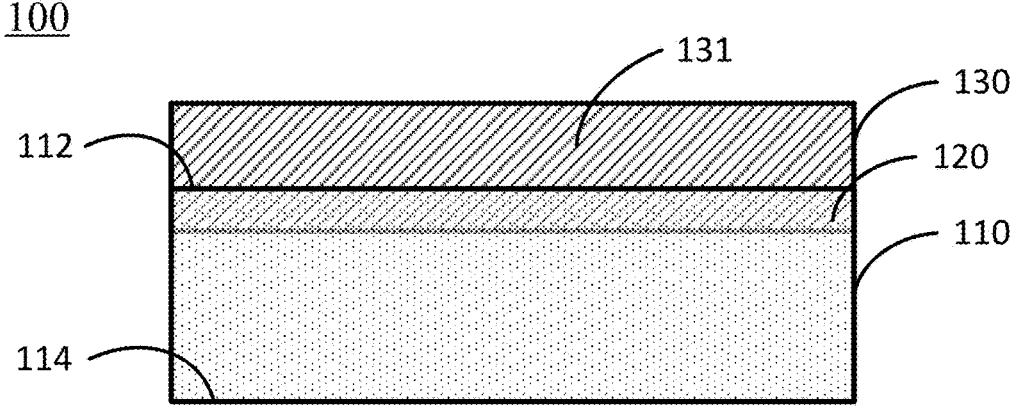
FIG. 1A schematically shows a two dimensional (2D) scaffold according to one embodiment of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

Typically, "nanoscopic-scale," "nanoscopic," "nanometer-scale," "nanoscale," the "nano-" prefix, and the like refers to elements or articles having widths or diameters of less than about 1 μm, preferably less than about 100 nm in some cases. Specified widths can be smallest width (i.e. a width as specified where, at that location, the article can have a larger width in a different dimension), or largest width (i.e. where, at that location, the article's width is no wider than as specified, but can have a length that is greater), unless pointed out otherwise.

As used herein, the term "Schwann cells" (also Gliocytus periphericus; named after physiologist Theodor Schwann) or neurolemmocytes refer to the principal glia of the peripheral nervous system (PNS). Glial cells function to support neurons and in the PNS, also include satellite cells, olfactory ensheathing cells, enteric glia and glia that reside at sensory nerve endings, such as the Pacinian corpuscle. There are two types of Schwann cell, myelinating and nonmyelinating. Myelinating Schwann cells wrap around axons of motor and sensory neurons to form the myelin sheath. Schwann cells are involved in many important aspects of peripheral nerve biology-the conduction of nervous impulses along axons, nerve development and regeneration, trophic support for neurons, production of the nerve extracellular matrix, modulation of neuromuscular synaptic activity, and presentation of antigens to T-lymphocytes.

As used herein, the term "HS-PEG-COOH and HS-PEG" refer to thiolated polyethylene glycol with or without acid terminal, respectively.

As used herein, the term "phosphate buffered saline" or "PBS" refers to a buffer solution commonly used in biological research. It is a water-based salt solution containing sodium phosphate, sodium chloride and, in some formulations, potassium chloride and potassium phosphate. The osmolarity and ion concentrations of the solutions match those of the human body (isotonic).

The description will be made as to the embodiments of the present disclosure in conjunction with the accompanying drawings. In accordance with the purposes of this disclosure, as embodied and broadly described herein, this invention, in one aspect, relates to 2D and 3D plasmonically active scaffolds and methods of fabricating and using same.

In certain embodiments, the present invention provides a well-defined system using different materials to replace current tissue grafts. In certain embodiments, a tissue graft system may include a biomaterial combined with biologically active molecules. The system may include a distinguishable three dimensional (3D) supporting structure called a scaffold.

Developing such a system requires deep understanding of the physiology of the infected tissue, the healing process, and any other factors that might assist and enhance the regeneration process. Therefore, designing an ideal scaffold is a challenging task that requires several features that should be present within the scaffold, such as a biocompatible structural matrix, ability for drug loading and releasing, providing the cells an environment in which they can attach easily, porosity, biodegradability, cell encapsulation, and tunable surface chemistry.

In certain embodiments, nanomaterials have been used for engineering bioactive scaffolds that have novel properties. However, these scaffolds may not provide the ideal environmental for cells to regenerate. Some of their shortcomings include a poor cell encapsulation environment, an absence of essential bioactive molecules within the structure, failing to provide a tunable surface chemistry, weak mechanical properties, and inability to supply drugs during the healing process. Therefore, in certain embodiments, a novel scaffold based on plasmonically active nanomaterials that fulfill all the requirements for cell proliferation and regenerated healthy tissue was prepared.

In certain aspects, the present invention relates to a two dimensional (2D) scaffold with plasmonic activity. FIG. 1A schematically shows a 2D scaffold according to one embodiment of the present invention. As shown in FIG. 1A, the 2D scaffold 100 includes a polymer layer 110 and a first nanoparticle layer 130 partially embedded on the polymer layer 110. The label 120 indicates the embedding of part of the nanoparticle layer 130 inside the polymer layer 130. The 2D scaffold 100 can be in any shape, for example, a cylindrical shape, a rectangular shape, or a spherical shape that conforms to a shape of an implant site. The size of the entire structure 100 can vary in order to match the size of the implant site that needs to be regenerated. In certain embodiments, the 2D scaffold 100 may be used as building blocks to form an implant.

The polymer layer 110 is made of a bio-compatible polymer material, such as chitosan, and the polymer layer 110 may be formed by a solvent casting procedure. In certain embodiments, the polymer layer 110 could be in form of porous structure, the porosity ratio of this substrate could be altered depending on the desire properties, and the porous size could be rage from 1 nm-1 mm. In certain embodiments, the thickness of the polymer layer 110 could be alter depending on desire properties, and may be ranged from about 1 μm to about 1 mm. The polymer layer 110 has a first side 112 and a second side 114 opposite to the first side 112. The polymer layer 110 can have different sizes and shapes as desired. In certain embodiments, the polymer layer 110 can be made as strips. For example, each of the polymer strips 110 can have a length of 0.005-50 cm, a width of 0.002-50 cm, and a thickness of 0.001-50 mm. In this embodiment, the polymer layer 110 is made of chitosan. In other embodiments, a wide range of synthetic biodegradable polymers can be used to form the polymer layer 110, including polyurethane (PU), polylactide (PLA), polyglycolide (PGA), poly(lactide-co-glycolide) (PLGA), poly(ε-caprolactone), polydioxanone, polyanhydride, trimethylene carbonate, poly(β-hydroxybutyrate), poly(g-ethyl glutamate), poly(desaminotyrosyl-tyrosine-hexyl ester (DTH) iminocarbonate), poly(bisphenol A iminocarbonate), poly(ortho ester), polycyanoacrylate, and polyphosphazene. In certain embodiments, a number of biodegradable polymers derived from natural sources such as modified polysaccharides (cellulose, chitin, dextran) or modified proteins (fibrin, casein) can be used to form the polymer layer 110.

The first nanoparticle layer 130 may be formed from gold, silver, or gold/silver of various shapes: nanorods and/or nanospheres, nanocage, nanoneedle, nanocavities, nanocubes, stars-like, doggybones, needles, etc. The first nanoparticle layer 130 is partially embedded in the first side 112 of the polymer layer 110. The part of the first nanoparticle layer 130 that is disposed inside the polymer layer 110 may be about ⅛-¾ of the total thickness of the polymer layer 110. In certain embodiments, about half of the first nanoparticle layer 130 is embedded inside the polymer layer 110. In certain embodiments, the first nanoparticle layer 130 may have only about one sheet of nanoparticles in the thickness direction, and the thickness of the first nanoparticle layer 130 may be about 12 nm. In other embodiment, the first nanoparticle layer 130 may include multiple sheets of nanoparticles stacked on the polymer layer 110, and the thickness of the first nanoparticle layer 130 is between approximately 0.001 mm and approximately 50 mm, but is typically less than 3 mm. In certain embodiments, the nanoparticles forming the first nanoparticle lay 130 may be metal nanoparticles or non-metal nanoparticles. The metal nanoparticles include gold nanorods, silver nanoparticles, iron nanoparticles, or copper nanoparticles. The non-metal nanoparticles include carbon nanoparticles, bone nanoparticles, hydroxyapatite (HAP) nanoparticles or other biocompatible nanoparticles.

The first nanoparticle layer 130 is attached with first functional groups 131. In one embodiment, the first functional groups 131 may be, for example, —COOH groups or —NH$_2$ groups. In certain embodiments, the first nanoparticle layer 130 has one type of functional groups. In other embodiments, the first nanoparticle layer 130 may include different type of functional groups.

Figure 1B:
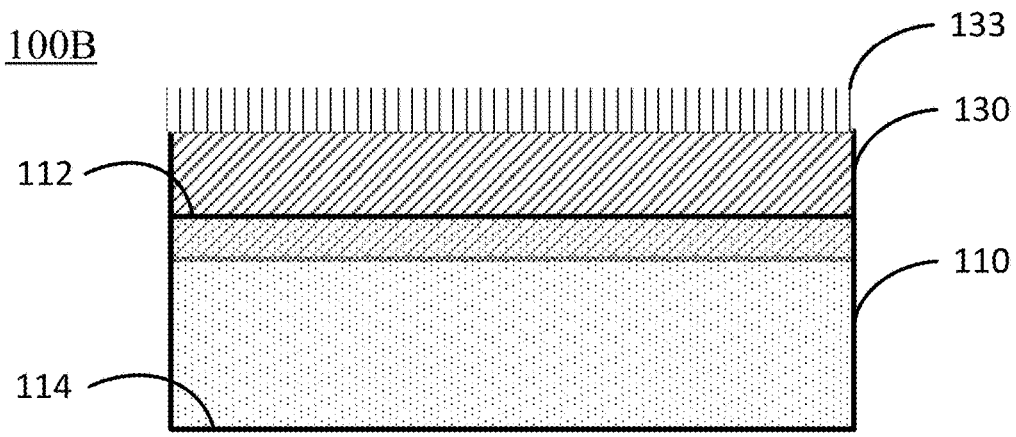
FIG. 1B schematically shows a 2D scaffold according to one embodiment of the present invention.

In certain embodiments, the thickness of the polymer layer 110 is about 3-500 nm, the thickness of the first nanoparticle layer 130 is about 1-120 nm. In certain embodiments, the thickness of the polymer layer 110 is about 6-180 nm, the thickness of the first nanoparticle layer 130 is about 2.5-60 nm. In one embodiment, the thickness of the polymer layer 110 is about 30 nm, the thickness of the first nanoparticle layer 130 is about 12 nm. Since the first nanoparticle layer 130 is partially embedded in the polymer layer 110, the total thickness of the 2D scaffold 100 is less than the sum of the thickness of the first nanoparticle layer 130 and the thickness of the polymer layer 110. For example, if the thickness of the polymer layer 110 is about 30 nm and the thickness of the first nanoparticle layer 130 is about 12 nm, half of the first nanoparticle layer 130 is embedded in the polymer layer 110, and the total thickness of the 2D scaffold is about 36 nm (30+12−6). FIG. 1B schematically shows a 2D scaffold 100B according to one embodiment of the present invention. As shown in FIG. 1B, a bioactive material 133 is attached to the upper surface of the first nanoparticle layer 130. In certain embodiments, the bioactive material 133 includes drugs, bioactive factors that promote growth of a tissue, or other bioactive agents. In certain embodiments, the bioactive material 133 is bonded to the first functional groups 131.

Figure 1C:
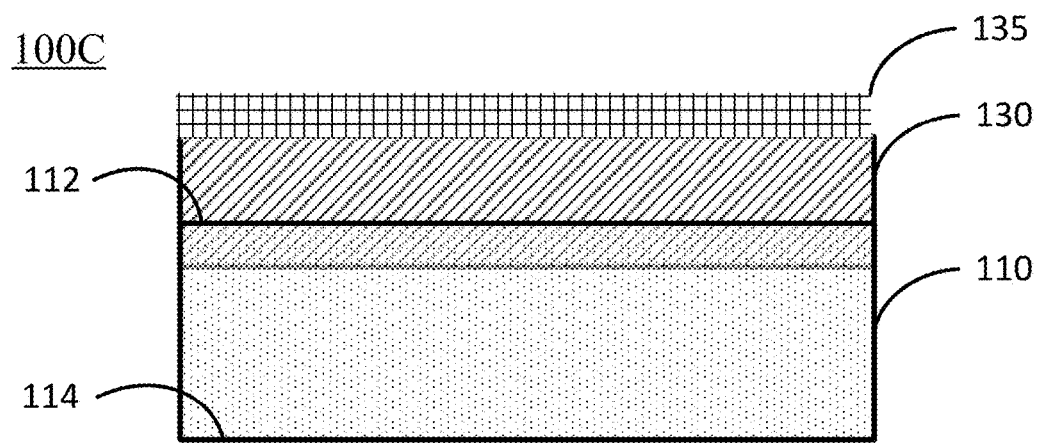
FIG. 1C schematically shows a 2D scaffold according to one embodiment of the present invention.

FIG. 1C schematically shows a 2D scaffold 100C according to one embodiment of the present invention. As shown in FIG. 1C, a structural material 135 is attached to the upper surface of the first nanoparticle layer 130. In certain embodiments, the structural material 135 includes, for example, one or more extracellular proteins. In certain embodiments, the 2D scaffold with the structural material 135 In certain embodiments, the structural material 135 is attached to the surface of the nanoparticle layer 130. In other embodiments, the structural material 135 may also be bonded to the functional groups 131.

Figure 1D:
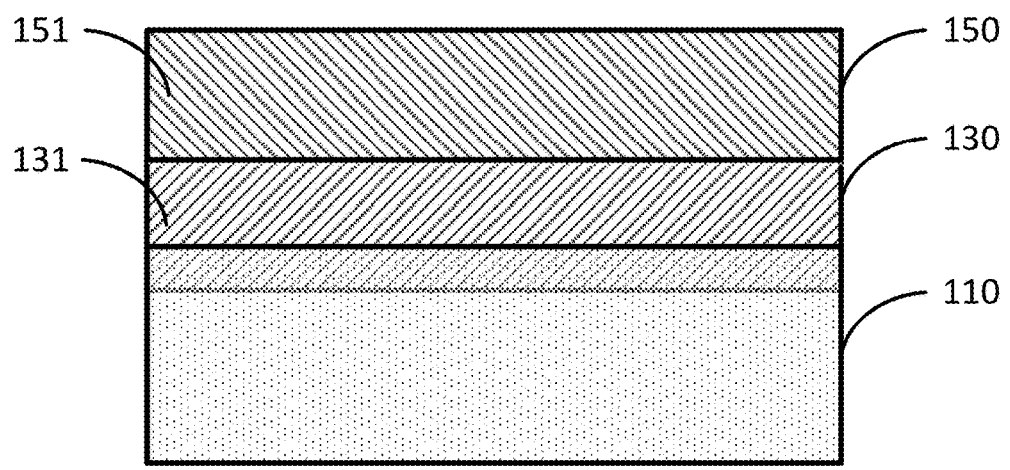
FIG. 1D schematically shows a 2D scaffold according to one embodiment of the present invention.

FIG. 1D schematically shows a 2D scaffold 100D according to one embodiment of the present invention. As shown in FIG. 1D, the 2D scaffold 100D further includes a second nanoparticle layer 150 disposed on the first nanoparticle layer 130. The second nanoparticle layer 150 has second functional groups 151. In certain embodiments, the first functional groups 131 and the second functional groups 151 are different type of functional groups, and the first nanoparticle layer 130 and the second nanoparticle layer 150 are attached to each other through the functional groups 131 and 151. For example, the first functional group 131 may be, for example —COOH group, and the second functional groups 151 may be, for example —NH$_2$ group, and the first functional groups 131 and the second functional groups 151 can be bonded to each other to form amide group (—CONH—). In certain embodiments, the 2D scaffold 100 may include more nanoparticle layers disposed on the second nanoparticle layer 150, such that the first nanoparticle layer 130, the second nanoparticle layer 150, and optionally one or more other nanoparticle layers are stacked sequentially. The adjacent two layers of nanoparticle layers may have different functional groups, so that they can be bonded together through the interactions between the different functional groups. The interactions between the functional groups in the adjacent layers may include covalent bonds such as amide bonds, and/or non-covalent interactions, such as π-π stacking effects, dipole-dipole inductions, and electrostatic interactions such as van der Waals forces, and hydrophobic effects, hydrogen bonds, ionic bonds. In one example, the 2D scaffold 100D includes multiple nanoparticles layers, the nanoparticle layers have alternatively the —COOH functional groups and the —NH$_2$ functional groups. When the 2D scaffold has multiple nanoparticle layers, only the bottom nanoparticle layer is embedded in the first side 112 of the polymer layer 110. In certain embodiments, about ⅛-¾ of the bottom one of the nanoparticle layers 130 is embedded inside the polymer layer 110. In one example, if there are three nanoparticle layers, the thickness of the polymer layer 110 (ranging from 1 nm to 5 mm) could be 30 nm and the thickness of the first nanoparticle layer 130 (ranging from 1 nm to 5 mm) could be about 12 nm, and half of the bottom nanoparticle layer is embedded in the polymer layer 110, then the total thickness of the 2D scaffold is about 60 nm (30+3×12−6). However, the thickness and the number of the layers can vary to address the required dimensions of the device.

In another aspect, the present invention relates to a 3D scaffold formed from the 2D scaffold described above.

In a further aspect, the present invention relates to methods of forming the 2D and the 3D scaffolds described above.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

EXAMPLE 1

Preparation of Functional Gold Nanorods

In certain embodiments, the nanoparticles of the nanoparticle layer 110 are gold nanorods (AuNRs), and the AuNRs were prepared according to the silver ion-assisted, seed-mediated method developed by Nikoobakht (Nikoobakht and El-Sayed, 2003). In certain embodiments, the preparation of the AuNRs is as follows. The seed solution was first prepared by mixing 5 ml of cetyl trimethyl ammonium bromide (CTAB) solution (0.2 M) with 5 ml of chloroauric acid (HAuCl$_4$, 0.0005 M), and then 600 ml of sodium borohydrid (NaBH$_4$, 0.01 M) were added with stirring for two minutes. To synthesize gold nanorods with an aspect ratio of around 3, 5 ml of CTAB (0.2 M) were mixed with 150 ml of silver nitrate solution (0.004 M), and then 5 ml of HAuCl$_4$ (0.001 M) were added and mixed. Afterward, 70 ml of ascorbic acid 0.0788 M were mixed with the solution, and finally, 12 ml of seed solution were added. The mixed solution was kept at 30° C. for 40 minutes without any further stirring. AuNRs were further purified twice by centrifugation at 10,000 rpm for 30 min to remove any excess reagents, and the precipitate includes the AuNRs.

The AuNRs were then processed with PEGylation with different functional groups. Specifically, AuNRs precipitates were re-dispersed in 2 ml of thiolated HS-PEG-NH$_2$ or HS-PEG-COOH (MW ~3000) solution (2 mg/ml of 2 mM NaCl) and vigorously stirred for 15 min. Then 1.8 ml of HS-PEG (MW ~5000) (2 mg/ml of 2 mM NaCl) stabilizer were added and kept in contact and stirring with the AuNRs at room temperature overnight. After that, any unbound thiolated PEG was removed by centrifugation at 10,000 rpm for 20 min twice. The PEG-covered nanorods were washed and re-suspended in 1xPBS solution and kept under 5° C. PEG-covered nanorods in solution were found to be highly stable for extended periods of time.

EXAMPLE 2

2D Scaffold Construction by Solvent Casting

Figure 2:
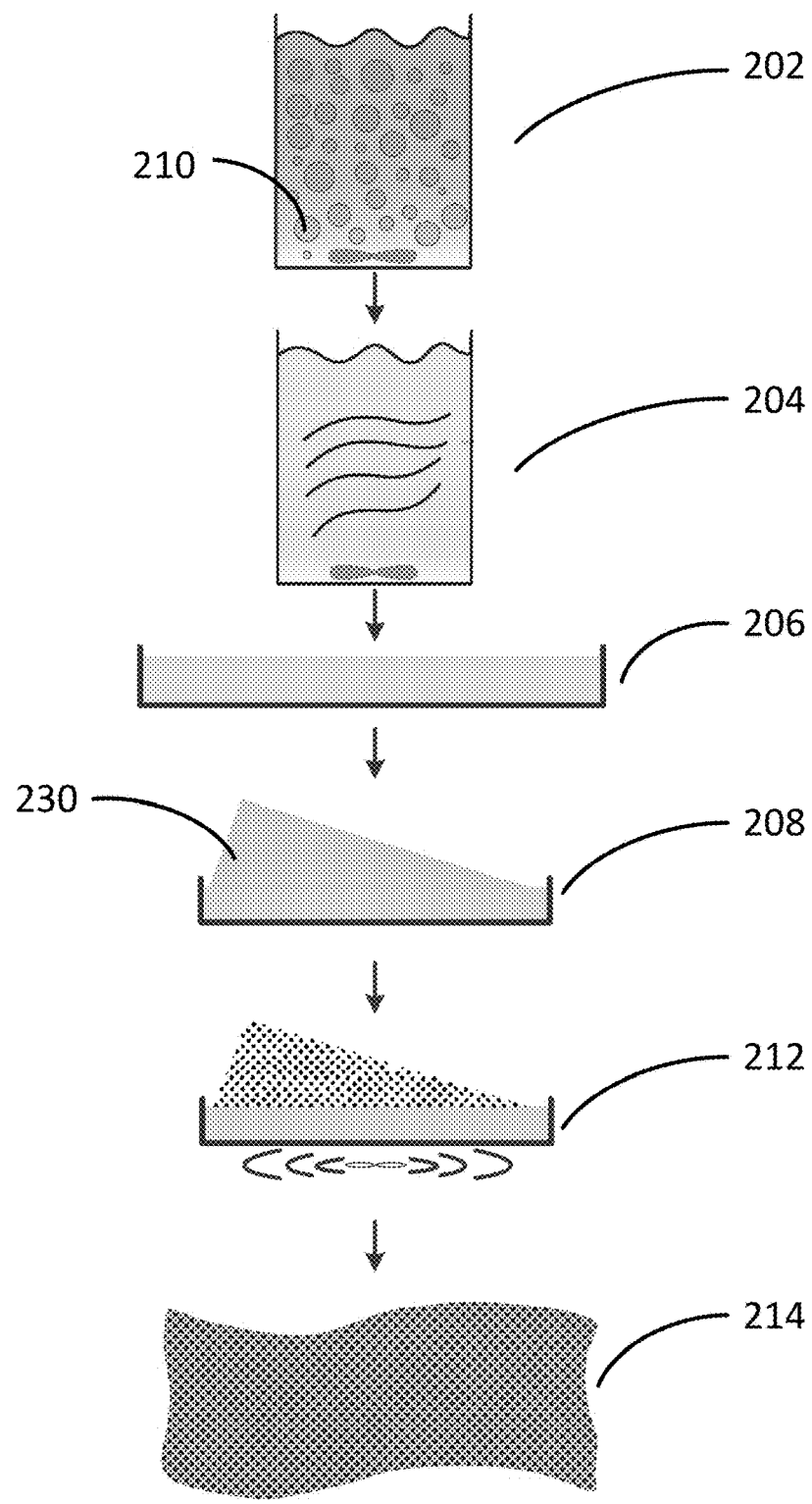
FIG. 2 schematically shows a procedure for producing a 2D scaffold according to one embodiment of the present invention.

In certain aspects, the present invention relates to a method for fabricating a 2D scaffold. FIG. 2 schematically shows a procedure for producing a 2D scaffold according to one embodiment of the present invention, which is exemplified by a solvent casting method using AuNR. As shown in FIG. 2, at procedure 202, 2 mg chitosan 210 is dissolved in 100 ml of 1% acetic acid using magnetic stirrer. At procedure 204, after performing the mixing for 24 hours, a uniform polymer solution is formed. At procedure 206, the uniform polymer solution were cast in a glass mold and then left to dry inside a furnace for 24 hours at 50° C. to obtain a completely dry polymer layer. At procedure 208, 1% acetic acid is applied over the dried sample. Then at procedure 212, 2 mg/ml aqueous solution of AuNR—X was added with a gentle orbital shaking to embed the AuNR—X on the surface. At procedure 214, the mold was left inside the furnace for 24 hours at 50° C. to get the complete dried thin film, that is, a 2D scaffold. The obtained 2D scaffold may have the structure as shown in FIG. 1, where a polymer layer 110 is covered with functionalized layer of AuNR—X (X=NH$_2$ or COOH). In certain embodiment, the method further includes subjecting the scaffold 100 to plasma treatment. For example, once completely dried, the scaffold 100 is placed into glass vials for storage. The scaffold 100 is plasma treated by a radio frequency (RF) plasma discharge device, under an environment of oxygen, nitrogen or a mixture of oxygen and nitrogen. In certain embodiment, the RF plasma treatment time is about 1-3 minutes. In certain embodiment, the plasma treated scaffold 100 is sterilized and sent for animal studies. The purpose of the plasma treatment is to break the surface bonds of the polymer. After plasma treatment, oxygen atoms "attach" to the surface, changing the surface energy of the surface such that the surface becomes more hydrophilic and has oxygen and nitrogen rich functional groups.

Figure 3A:
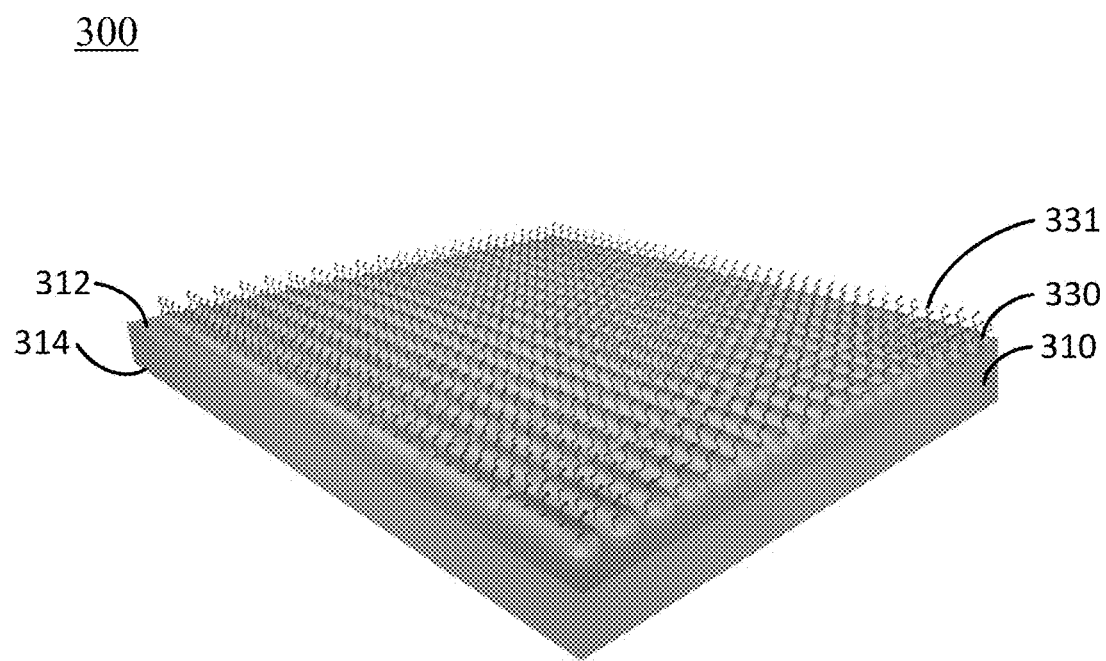
FIG. 3A schematically shows a two dimensional (2D) scaffold according to one embodiment of the present invention.

FIG. 3A schematically shows a structure of a 2D scaffold. The 2D scaffold 300 includes a polymer layer 310 and a nanoparticle layer 330. The polymer layer 310 has a first side 312 and a second side 314 opposite to the first side 312. The nanoparticle layer 330 is partially embedded in the first side 312. The nanoparticle layer 330 has functional groups 331 attached to the outer surface of the nanoparticles.

Figure 3B:
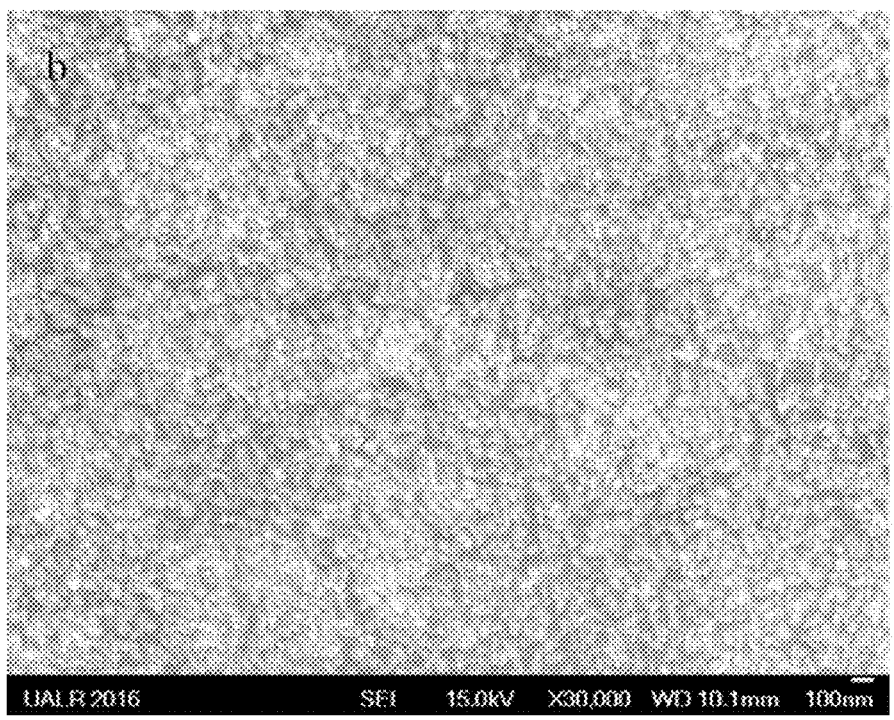
FIGS. 3B and 3C show Scanning Electron Microscopy (SEM) images of a 2D scaffold according to one embodiment of the present invention.
Figure 3C:
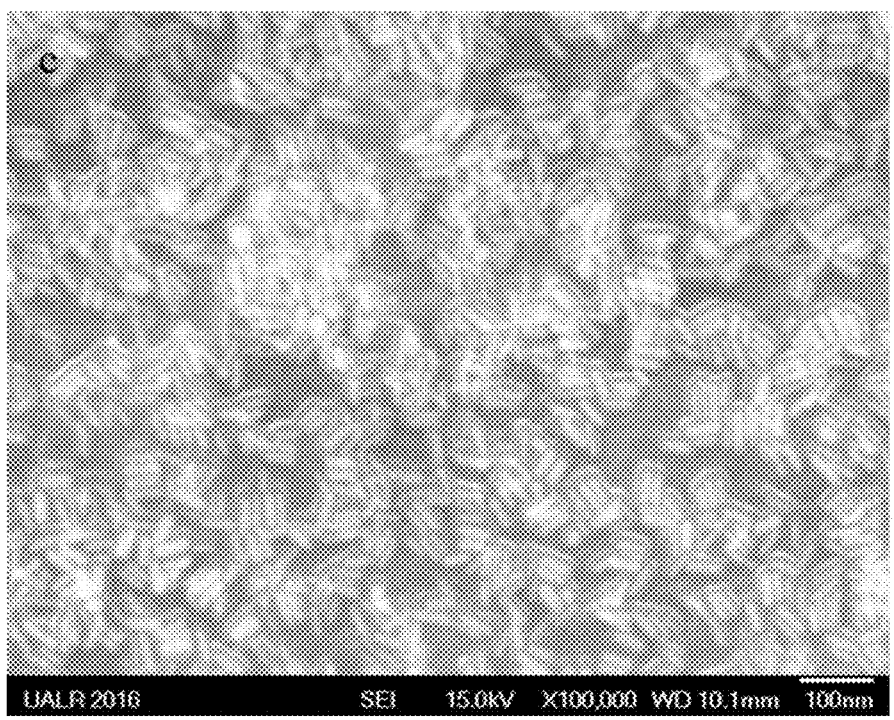

FIGS. 3B and 3C show Scanning Electron Microscopy (SEM) images of the 2D scaffold fabricated according to the procedures described above. As shown in FIGS. 3B and 3C, the AuNRs occupy a substantial amount of the surface of the polymer layer, but may not fill the surface of the polymer layer completely. The AuNRs are mostly disposed along the horizontal surface of the polymer layer. The dimensions of the majority of the AuNRs may be approximately 12 nm×36 nm.

EXAMPLE 3

Construction of Nanoparticles Bioactive Layer Over Functionalized Biodegradable Substrate Different nanoparticles can be used as bioactive layers such as (gold based nanostructures with a variety of architectures and shapes: nanorod, nanospheres, nano-cavities, nano-needles, cubes, etc.), starting the construction required surface modification of the nanoparticles. Strong semi-covalent Au—S bonds, can be used for the anchoring of the thiol molecules over Au surface.

Figure 4:
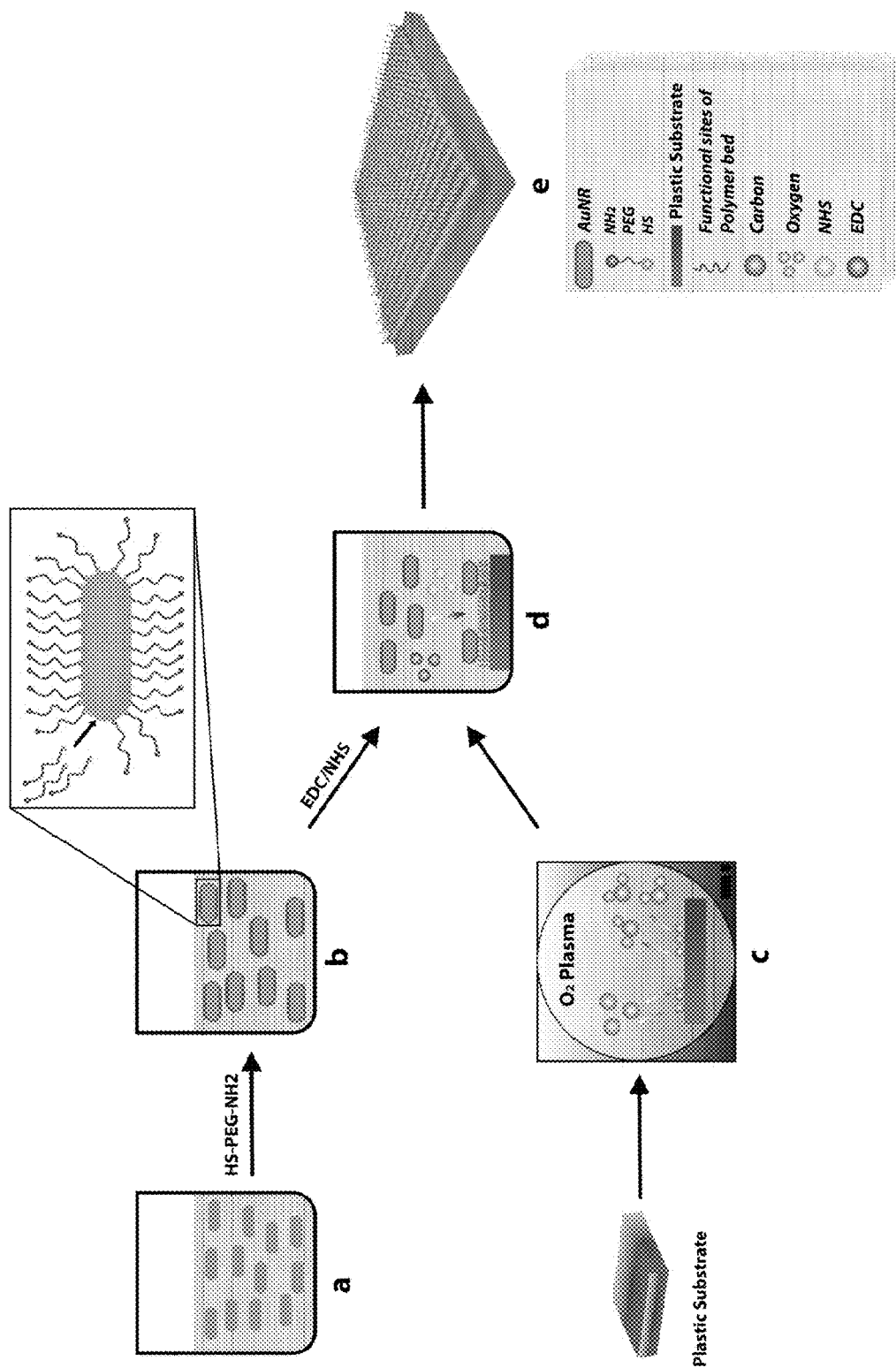
FIG. 4 schematically shows a procedure for constructing a nanoparticles bioactivity layer over functionalized biodegradable substrate according to one embodiment of the present invention.

Specific example using AuNRs as building block for the construction of the bioactive layer is described below in reference to FIG. 4. FIG. 4 schematically shows a procedure for constructing a nanoparticles bioactivity layer over functionalized biodegradable substrate according to one embodiment of the present invention. In FIG. 4, possible procedure used to prepare AuNRs 2D substrate includes: (a) AuNRs preparation; (b) AuNR functionalization; (c) O2 plasma treatment; (d) assembling the functionalized AuNRs over the polymer bed; and (e) washing with DI water, and then treated with ethanol and UV for sterilization. Specifically:

1. The purified AuNRs (FIG. 4,a) were functionalized with HS-PEG-NH$_2$ (FIG. 4,b) to modify their surface chemistry. Specifically, AuNR precipitates were re-dispersed in a certain volume of (2 mg/ml) HS-PEG-NH$_2$ solution and stirred vigorously.

2. Certain volume of HS-PEG (2 mg/ml) stabilizer were added and stirred with the AuNRs at room temperature overnight and then kept at 4° C. for 24 hours before use. After that, any unbound thiolated PEG was removed by centrifugation. The resulting sediment of PEG-covered nanorods were re-suspended in 1xPBS solution (2 mg/ml) and kept at 4° C.

3. Different biodegradable polymer might use as the substrate to coat functionalized AuNRs such as polyurethane, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly (desaminotyrosyl-tyrosine-hexyl ester (DTH) iminocarbonate), poly(bisphenol A iminocarbonate), poly (ortho ester), polycyanoacrylate, and polyphosphazene. This substrate could be in form of porous structure, the porosity ratio of this substrate could be alter depend on the desire properties. Prior to coating, the substrate may be treated with oxygen plasma (100 mTorr O2 with 65 W) for a variable time period of up to 30 minutes (FIG. 4,c). This step produced a more hydrophilic surface and induced reactive oxygen functional groups.

4. NHS/EDC conjugation assay was performed to cover the substrate with a coating of AuNRs-HS-PEG-NH$_2$ (FIG. 4,d). Briefly, 10 mg/mL stock solutions of EDC and NHS each were prepared in 1xPBS. The I2-treated Thermanox cover slips were placed in a 24-well plate, and 2 ml of 2 mg/ml functionalized AuNRs were added to each substrate, followed by the addition of 228 µl of EDC solution and 112 µl of NHS solution. Using an orbital shaker, the mixture was gently shaken at 100 rpm for 4 hours in order to achieve full conjugation. The excess liquid above the substrate was removed, and the substrate was washed extensively with DI water to remove any unbound AuNRs-SH-PEG-NH$_2$ molecules.

5. The first bioactive layer of AUNRs-SH-PEG-NH$_2$ could be modify by adding second layer of AUNRs using the layer-by-layer approach, lead to construction of Multilayers AuNRs-X OR AuNRs-Y (X=SH-PEG-NH$_2$), (Y=SH-PEG-COOH) on the functionalized substrate. Briefly, 2D scaffold covered with functionalized layer from AUNR—X was used as building block for this structure, for the second layer construction, AuNRs functionalized with Y were re-dispersed from the last centrifugation in 1xPBS to get 2 mg/ml as final concentration, 2 ml of AuNRs-Y were added to the building block substrate, followed by adding 228 µl of EDC, and 112 µl of NHS, and then the mixture were gently shaken at 100 rpm for 24 hours. After this period, the excess solution was removed, and then the building block substrate was extensively washed several times with DI water to remove the unbounded AuNRs-Y from the building block substrate. For more layers construction, a repeating of 24 hours conjugation reaction between a covered layer of AuNRs-X with 2 ml of 2 mg/ml AuNRs-Y and vice versa based on the last layer, which is covered the substrate.

6. Converting the 2D structure of the bioactive substrate achieved by these steps: first, integrate the 2-D Multilayers AuNRs substrate into a cylindrical structure with conduit like structures. Prepare stripes of 2-D Multilayers AuNRs functionalized substrates, these stripes should be in sufficient numbers and width in order to result in a structure of desired dimensions. Filling the conduit-like structure uniformly with these strips in layer-by-layer approach, where each strips should fit the exact section of the conduit, which is fit with its width. Apply a small amount of proper solvent over the whole structure, fouled by applying pressure gently to allow integration of the 2-D multilayers AuNRs functionalized substrates with each other to obtain the desired 3D architecture.

EXAMPLE 4

Multiple Layers AUNRS on the Functionalized Substrate

Figure 5:
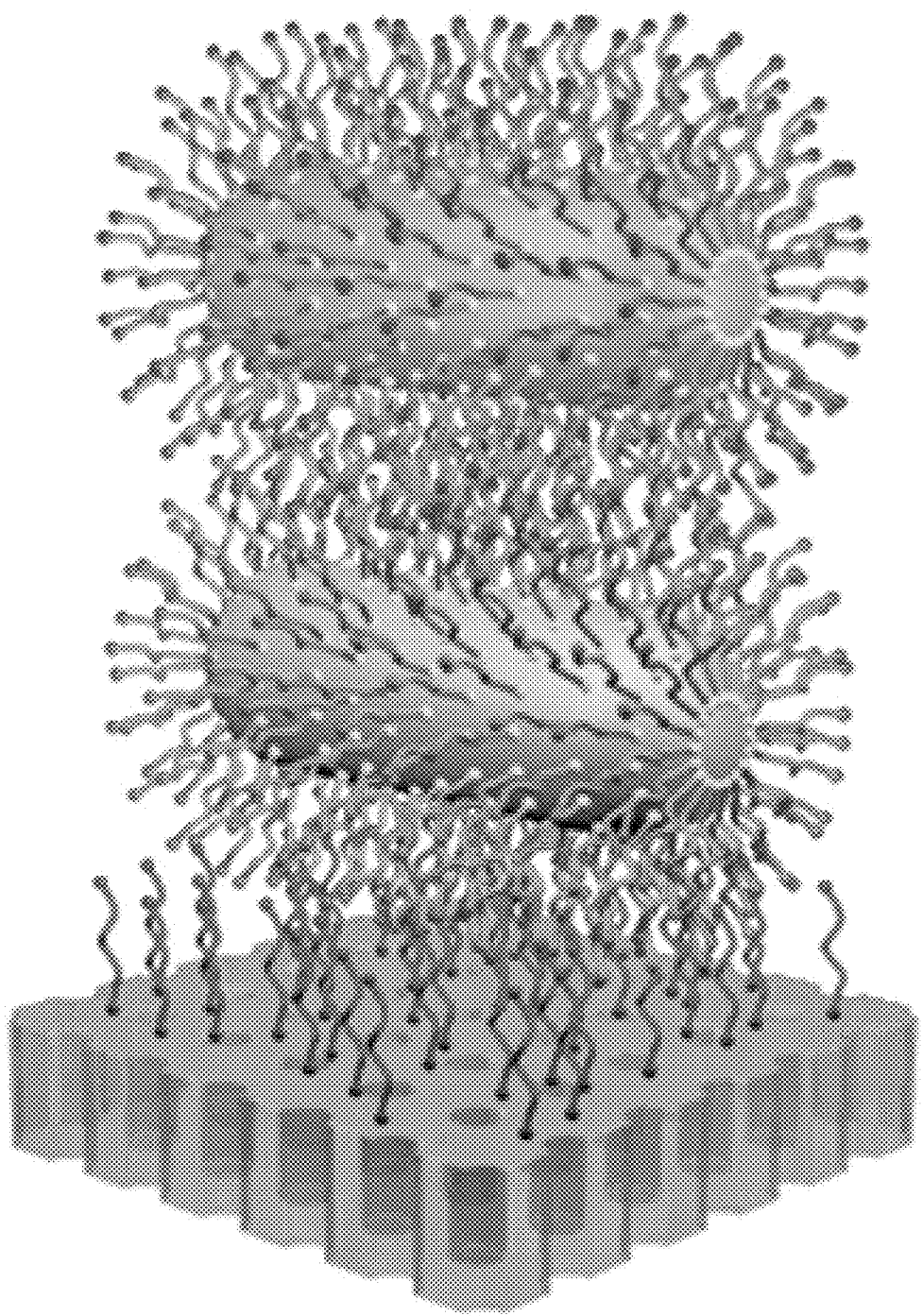
FIG. 5 schematically shows a multilayer 2D scaffold according to one embodiment of the present invention.

In certain aspects, the present inventions related to a 2D scaffold with multiple nanoparticle layers. FIG. 5 schematically shows a multilayer 2D scaffold according to one embodiment of the present invention. A layer-by-layer approach may be used for the construction of multilayers AuNRs on the functionalized substrate as shown in FIG. 5. Briefly, 2D scaffold covered with functionalized layer from AuNR-s-COOH or AuNRs-NH$_2$ (depends on the desire properties, where the top and the last layer deposit will be the controller of what the first layer could be) was used as building block for this structure, where this structure were previously explain in examples 2 and 3. This structure consists of polymer layer. This layer could be in form of a porous structure, the porosity ratio of this substrate could be altered depend on the desire properties the porous size could be rage from 1 nm-1 mm. The layer thickness could be altered depending on the desire properties ranging from 1 µm-15 mm. On the top of this polymer layer, a nanomaterial sheet were deposit with thickness passed on the type of the nanomaterial, within this example the thickness of the sheet is around 12 nm, but could vary from 1 nm to 5 mm. For the second layer construction, AuNRs functionalized with NH$_2$ were re-dispersed from the last centrifugation in 1xPBS to get 2 mg/ml as final concentration. 2 ml of AuNRs-NH$_2$ were added to the building block substrate, followed by adding 228 µl of 1-ethyl-3-(3-dimethylaminopropyl)carbodiimide (EDC), and 112 µl of N-hydroxysuccinimide (NHS), and then the mixture were gently shaken at 100 rpm for 24 hours. After this period, the excess solution was removed, and then the building block substrate was extensively washed several times with DI water to remove the unbounded AuNRs-NH$_2$ from the building block substrate. For more layers construction, a repeating of 24 hours conjugation reaction between a covered layer of AuNRs-NH$_2$ with 2 ml of 2 mg/ml AuNRs-COOH and vice versa based on the last layer, which is covered on the substrate.

EXAMPLE 5

Plasmonically Active Scaffold

The 2D scaffold with one or more nanoparticles layers as described above show plasmonic activity. In certain embodiments, the plasmonically active scaffold may be used to improve axonal motility and extension.

In certain embodiments, the active plasmonic nanoparticles are used to enhance axonal motility and extension. This enhancement is particularly coordinate with a moderate increase in the intracellular calcium (Ca$^{2+}$) concentration (Henley and Poo, 2004). It was believed that the excitation of the active plasmonic surface would produce transient heating, which in turn could change the membrane capacitance and activate a very specific sensitive ion channels located in the cell membrane (Paviolo et al., 2014).

Figure 6:
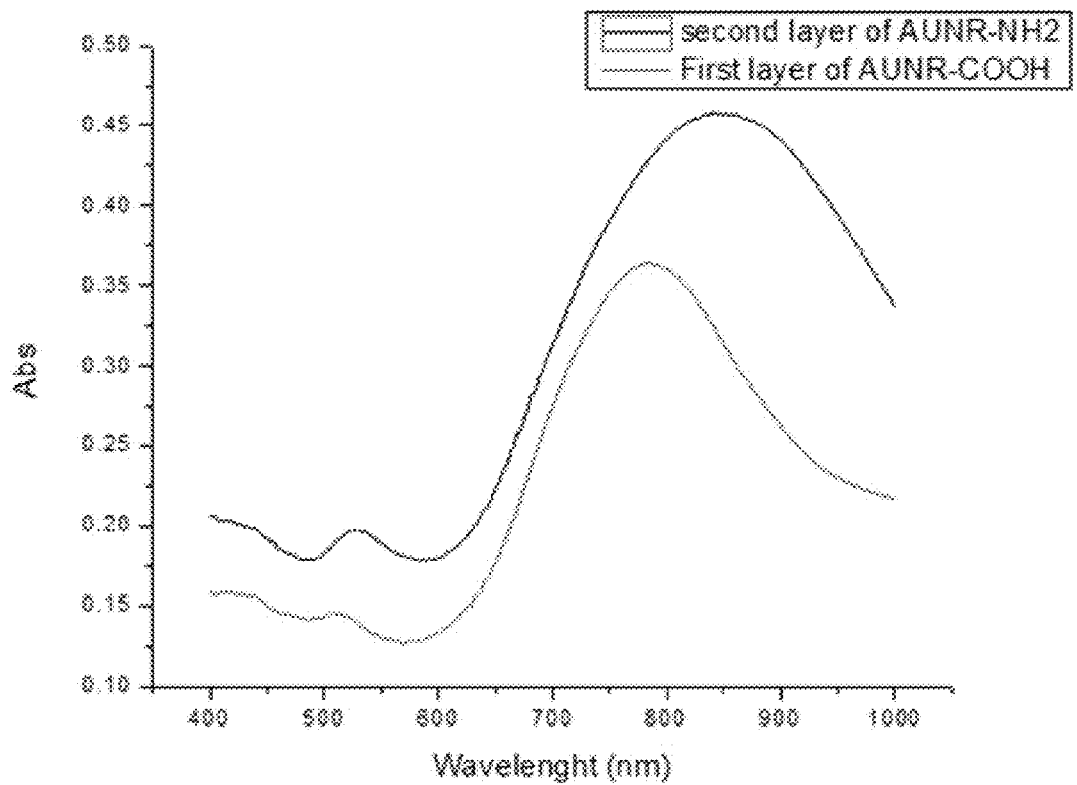
FIG. 6 shows UV-VIS spectra of 2D scaffolds according to one embodiment of the present invention.

In certain embodiments, the present invention relates to a 3D plasmonic active scaffold that is constructed from multilayers AuNRs on the functionalized substrate. This 3D scaffold has both transverse and longitudinal plasmons resonances peaks located at wavelength of 512 nm and 780 nm sequentially in the case of monolayer as shown in FIG. 1 while these peaks will shift significantly more layers were added, as shown in FIG. 6.

EXAMPLE 6

Basal Lamin (BL)-Like Structure on the Functionalized Scaffold

In certain aspects, the present invention relates to a 2D scaffold mimicking a basal lamina (BL) structure. In certain embodiments, a BL-like structure may be constructed on the functionalized scaffold. Biomimetic extracellular matrix (ECM) microenvironment is a quite challenge in the field of tissue engineering. Different proteins are involved in ECM structure such as laminin (LN), perlecan (PN), collagen, nidogen, and fibronectin (Fn) (Barros et al., 2011). In the nervous system, some of these proteins combine to form unique substrate structure called basal lamina (BL). BL promotes cell attachment, migration, and crawling. In the case of the peripheral nervous system, BL was found as surrender for Schwann cells, perineuria, neuromuscular junctions, nodes of Ranvier, and individual muscle fibers (Birch, 2011). The architecture structure of BL is constructed from two primary networks of laminin and collagen. In this structure the laminin presented the base layer, flowed by multilayers of a sheet-like polygonal network constructed by assembling of collagen molecules in the form of dimers, the collagen dimer consists from two combining two collagen heads molecules, followed by tail interaction of adjoining dimers. The collagen networks interact with laminin network covalently via functionalized sites located on both laminin and collagen.

The other proteins are involved to form this complex networks via chemical interaction between functionalized sites of this networks and functionalized sites of these proteins (Vella, 1994).

Figure 7A:
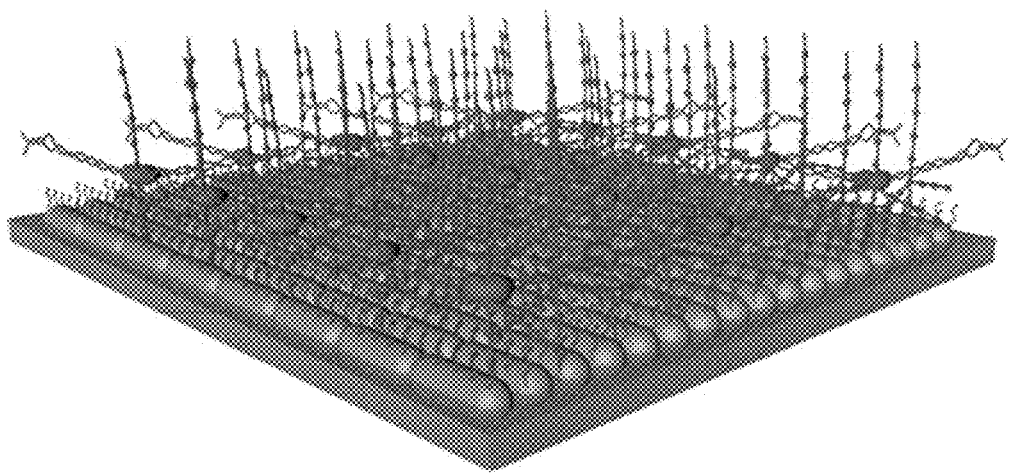
FIGS. 7A and 7B schematically show basel lamina-like layers covered 2D scaffold according to one embodiment of the present invention.
Figure 7B:
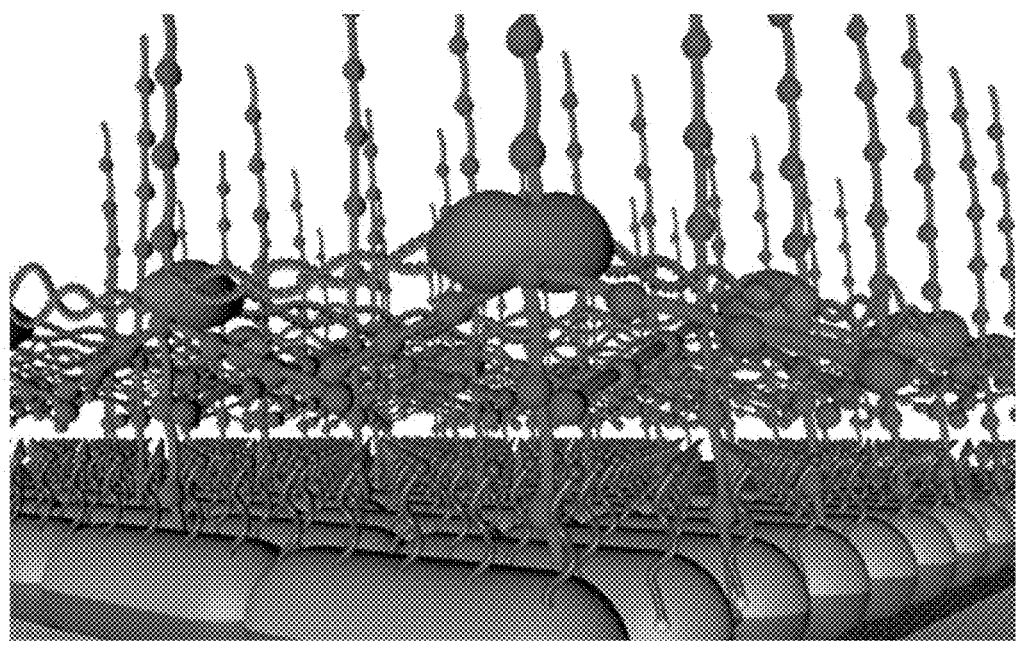
Figure 8A:
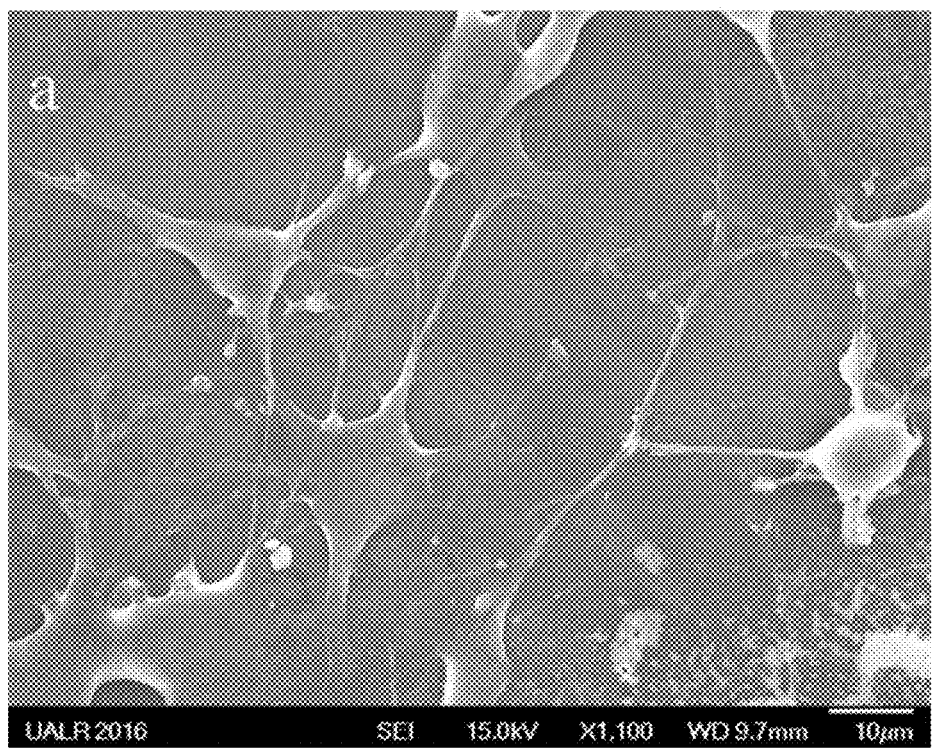
FIGS. 8A-8C show SEM images of Schwann cells over a 2D scaffold according to one embodiment of the present invention.
Figure 8B:
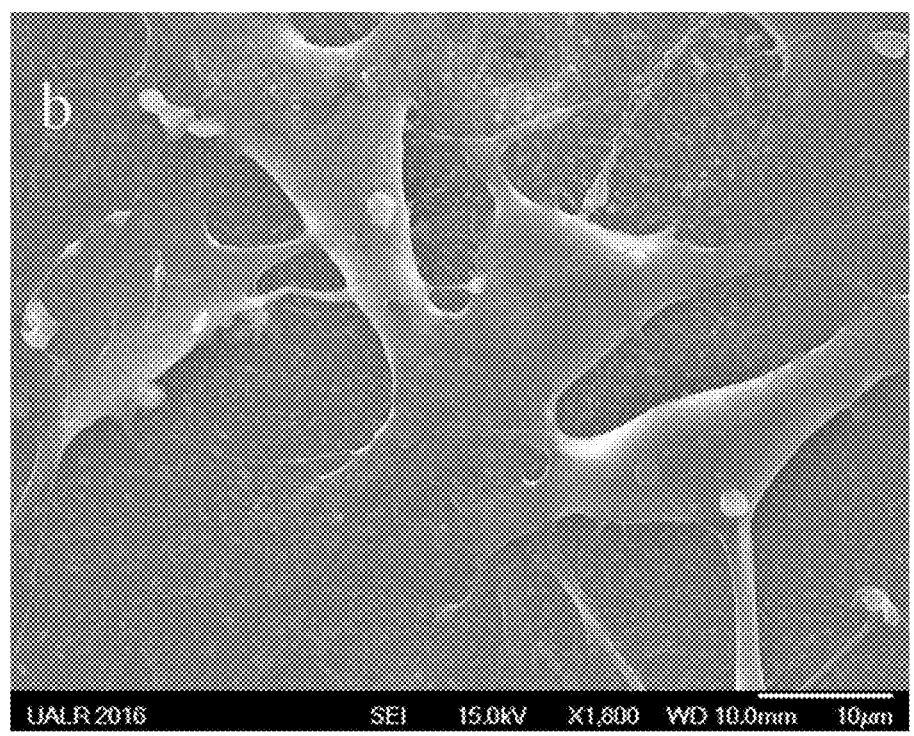
Figure 8C:
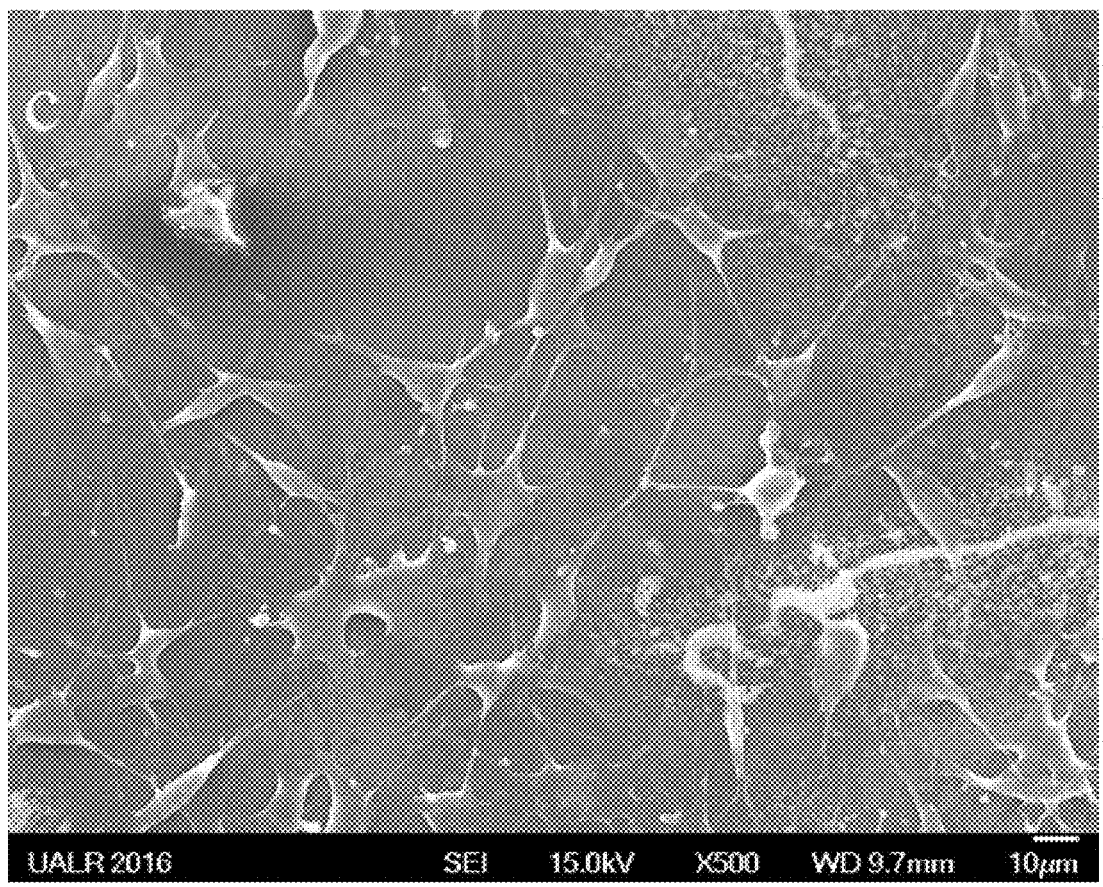
Figure 9A:
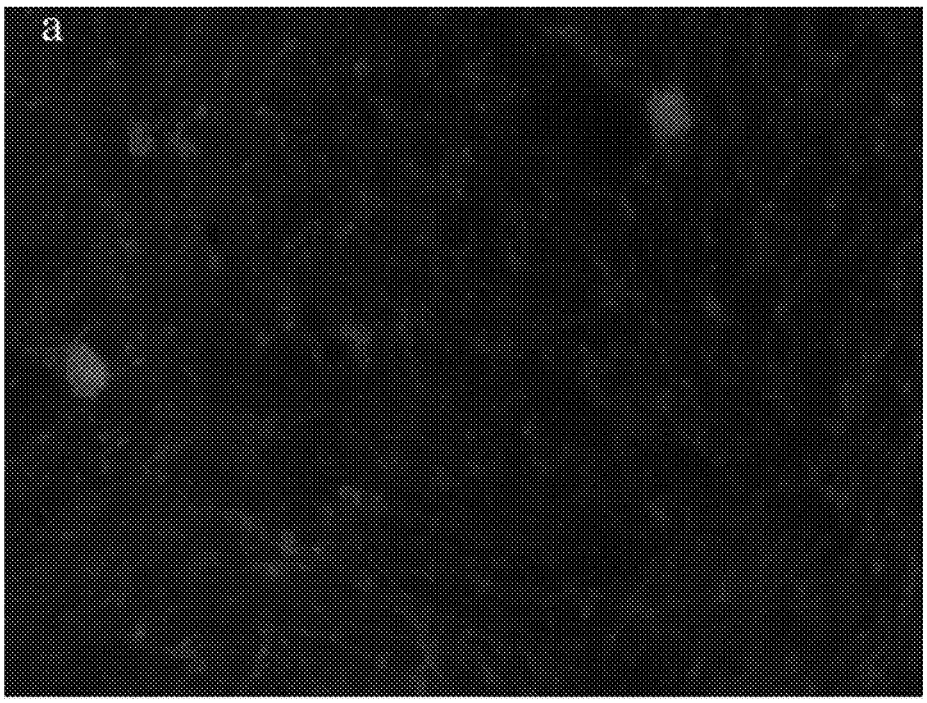
FIGS. 9A and 9B show immunofluorescence staining image of cytoplasmic of Schwann cells according to one embodiment of the present invention.
Figure 9B:
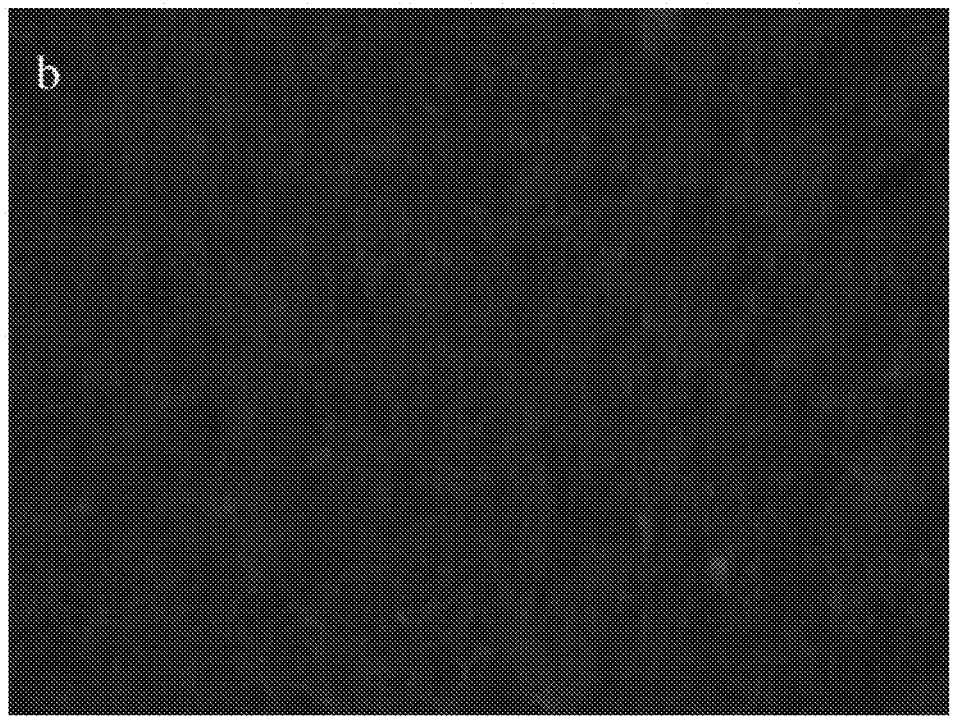

Understanding the function and the arrangement of BL allow us to mimic these structure. In certain embodiments, the present invention presented the ability to mimic BL structure by the chemical combining of essential components involves the construction of BL structure as shown in FIGS. 7A and 7B. Different proteins can be loaded over the involved in ECM structure such as laminin (LN), perlecan (PN), collagen, nidogen, and fibronectin (Fn), the loading procedure based on the covalent interaction between the free functional sites of the 2D scaffold the free functional sites of the proteins, for example if the 2D scaffold have COOH free functional sites, this sites will be link to the $NH_2$ free functional sites of the proteins by using EDS/NHS assay. This technique accomplishes by loaded multi extracellular proteins on the functionalized 2D-scaffold. The assembling of this structure is based on existing of different functional groups within the multilayers AuNRs-X, and by carefully understands the conjugation interaction between functional groups of AuNRs-X and the functional sites of BL proteins.

Achieving this unique structure represents a breakthrough in the field of tissue engineering, where besides enhancing cell attachment, migration, and crawling accomplish by this structure, it will also open a new route in cell therapy to treat nerve defect. The ability of cells to survive and its tendency to attach to this structure have been investigated through seeded a rat Schwann cells RT4-D6P2T for a period. Cells adhesion and attachment profiles were analyzed by using SEM and immunofluorescence assay, as shown in FIGS. 8A-8C and FIGS. 9A and 9B, respectively. Both analysis tools show that Schwann cells integrate and interact well through the net like structure over the scaffold, such interaction give indication about the biocompatibility of the AuNRs-X scaffold which make it a perfect candidate to incubate the required cells within 3D-structure of multilayers AuNRs-X scaffold. These primary results open a new route to design a promising device for provides a suitable proliferation environment for essential and supportive cells to grow simultaneously and synergistically.

EXAMPLE 7

Enhancing Bio-Functionality of 2D Scaffold by Converting it to Local Drug Delivery Device In certain aspects, the present invention provides a local drug delivery device from a bio-functional 2D scaffolds. In certain embodiments, designing a bioactive scaffold as local drug release device is the ultimate goal in the field of tissue engineering. The ability to incubate the drugs within the 3D-structure, beside a homogeneous distribution, represents quite a challenge in the design of a drug release device. Furthermore, the releasing profile of the incubated drug should be in balance state with a degradation rate of the scaffold, and both of them should be terminated at the time of total recovery (Ramburun et al., 2014; Rousseau et al., 2014). Different neurotrophic factors have been used in the treatment of nerve injuries such as brain-derived neurotrophic factor (BDNF), nerve growth factor (NGF), neurotrophin-3 (NT-3), FGFs and glial growth factor (GGF) (Schmidt and Leach, 2003). Analysis of the chemical structure of the neurotrophic factors will facilitate incubation procedure for these drugs within the structure of the scaffold. The existing of different functional group on the surface of the multilayers AuNRs-X scaffold gives us a simple technique to load one or different neurotrophic factors within the 3D-structure of the scaffold. The loading procedure is based on conjugates reaction between the functional groups of AuNRs-X and functional sites of the candidate drug.

Figure 10:
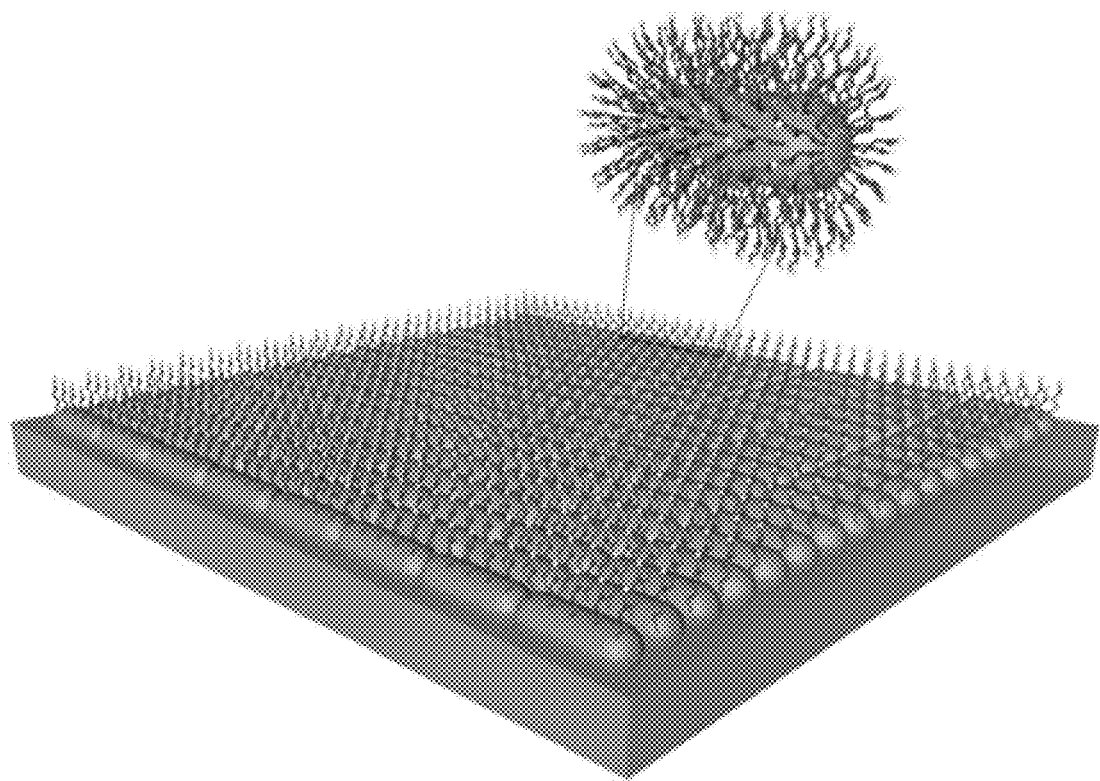
FIG. 10 schematically shows incubation of drug within a 2D scaffold according to one embodiment of the present invention.

FIG. 10 schematically shows incubation of growth factors (NGF, EGF, etc.), antibiotics, within a 2D scaffold according to one embodiment of the present invention. As shown in FIG. 10, a 2D scaffold is formed with a polymer layer and a nanoparticle layer. The nanoparticle in the nanoparticle layer is attached with functional groups, and drugs are linked to the functional groups. The linkage between the functional groups and the drugs may be stable covalent bond or non-covalent bond.

Figure 11:
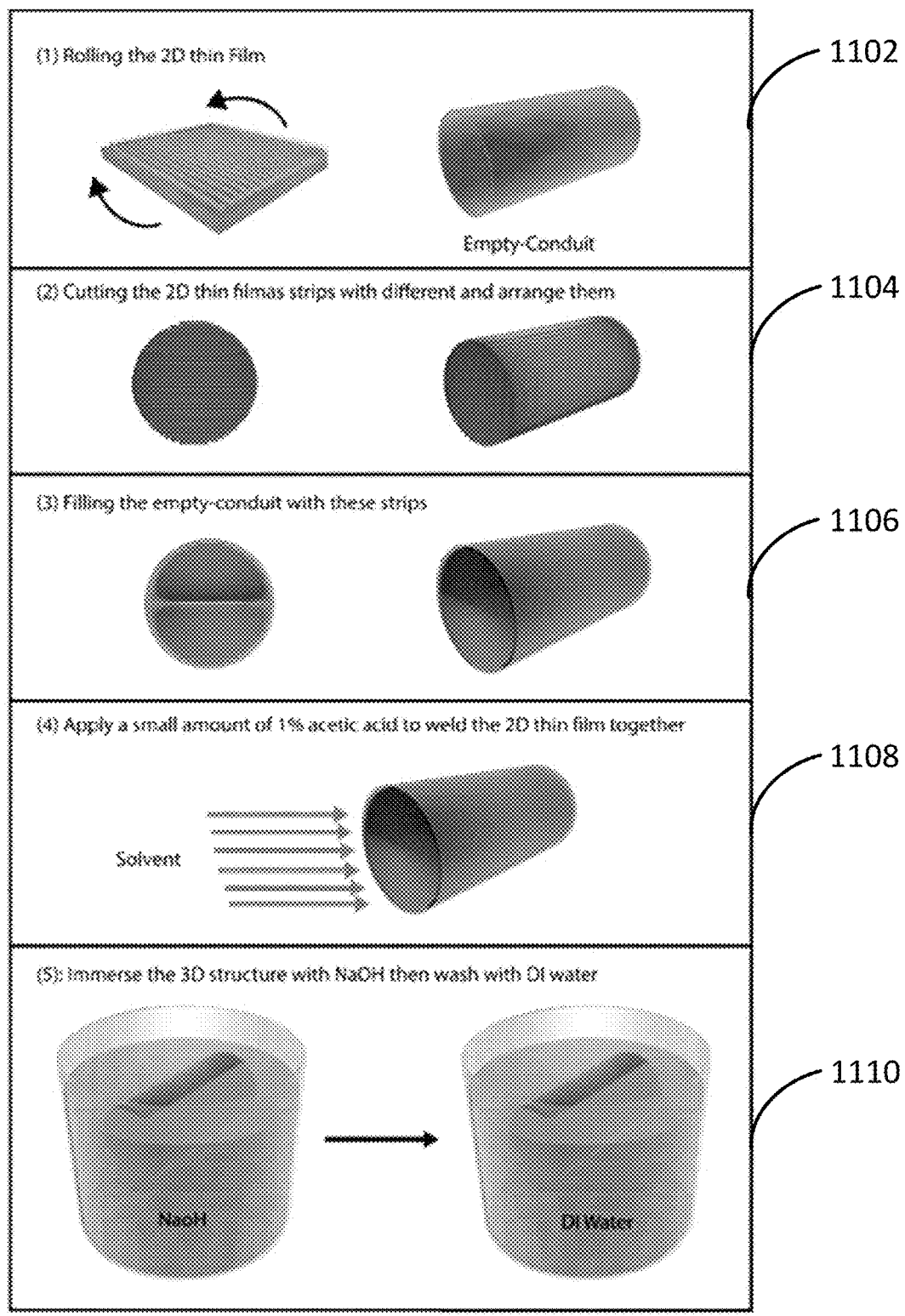
FIG. 11 schematically shows a procedure for producing a 3D scaffold according to one embodiment of the present invention.

In certain aspect, the present invention relates to a 3D scaffold structure by combining the multi-substrate layers as described above. FIG. 11 schematically shows a procedure for producing a 3D scaffold according to one embodiment of the present invention.

EXAMPLE 8

Combine Multi-Substrate Layers in One 3D Scaffold Structure

As shown in FIG. 11, at procedure 1102, the 2-D multilayers AuNRs substrate is rolled to have conduit like structure.

At procedure 1104, 2-D multilayers AuNRs functionalized substrates are prepared, and the 2-D multilayers AuNRs functionalized substrates are cut as stripes to have sufficient numbers of these stripes with different width.

At procedure 1106, the conduit-like structure is filled uniformly with these strips in layers style, where each strips should fit the exact section of the conduit, which is fit with its width.

At procedure 1108, a small amount of 1% acetic acid is applied over the whole structure, fouled by applying pressure genteelly to allow welding the layers of 2-D multilayers AuNRs functionalized substrates with each other.

Figure 12:
FIG. 12 schematically shows a side sectional view of a 3D scaffold according to one embodiment of the present invention.
Figure 13:
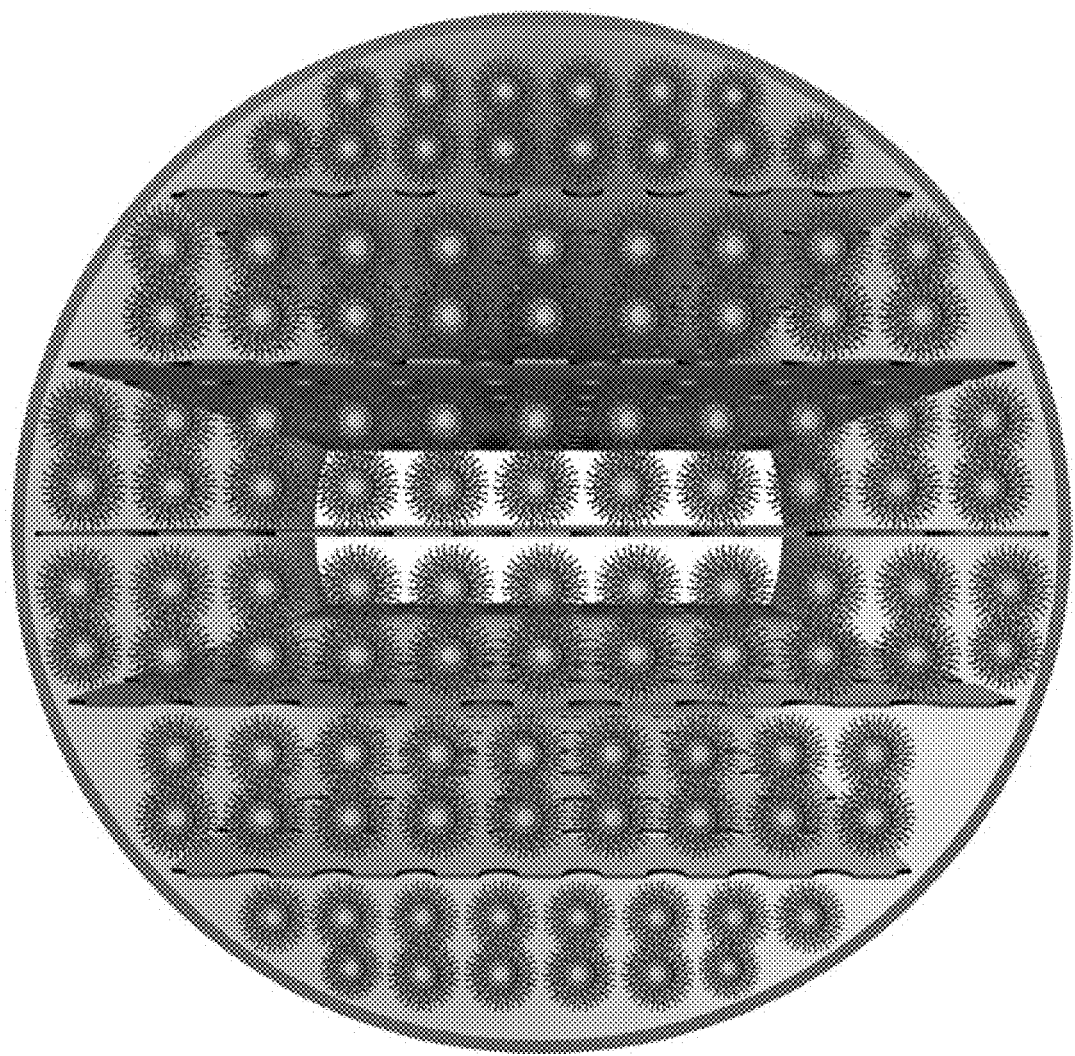
FIG. 13 schematically shows a cross-sectional view of a 3D scaffold according to one embodiment of the present invention.

At procedure 1110, the 3-D structure is immersed inside 0.5 M of NaOH for 30 minutes, to stabilize the structure. Then, the 3-D structure was washed extensively with deionized (DI) water for several times, and stored in healthy environmental for further use. FIGS. 12 and 13 shows the 3-D structure of active plasmonic scaffold obtained by the method described above in FIG. 11. Specifically, FIG. 12 schematically shows a side sectional view of a 3D scaffold according to one embodiment of the present invention, and FIG. 13 schematically shows a cross-sectional view of a 3D scaffold according to one embodiment of the present invention.

In summary, certain embodiments of the present invention provides for the first time an ideal design for a bioscaffold that has the ability to treat different tissue injury such as bone, nerve, as well as soft tissue damage. The structures shown in the above examples can be combined to meet the requirement of regenerating the damaged tissue. For example, a 2D scaffold may include multiple nanoparticles layers as shown in FIG. 4, and one or more of the multiple layers can be attached with bioactive agents such as drugs.

Certain embodiments of the 2D and 3D scaffolds of the present invention, among other things, have unique features that can be summarized as follows:

1. The ability to tune up the surface chemistry of the active layers to modify (functionalized) with different biological molecules.

2. Has surface plasmon active nanomaterials, which is potentially useful for enhancing the nerve injury regeneration process.

3. Easy to load with drugs so as to become a local drug releasing vehicle, such as growth promoters, chemotherapy agents, and antimicrobials.

4. Tunable surface chemistry which make the scaffold a perfect candidate to mimic the Basal Lamin-like structure, by building layers of extracellular proteins over the active layer of the scaffold, this structure fundamentally represents a key for cells adhesion, survival and growth 5. Provide a suitable proliferation environment for essential and supportive cells to grow simultaneously and synergistically, such as stem cells, and Schwann cells.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

LISTING OF REFERENCES

ALGHAZALI, K. M., NIMA, Z. A., HAMZAH, R. N., DHAR, M. S., ANDERSON, D. E. & BIRIS, A. S. 2015. Bone-tissue engineering: complex tunable structural and biological responses to injury, drug delivery, and cell-based therapies. *Drug Metabolism Reviews*, 47, 431-454.

BARROS, C. S., FRANCO, S. J. & MULLER, U. 2011. Extracellular matrix: functions in the nervous system. *Cold Spring Harb Perspect Biol*, 3, a005108.

BAYER, I. S., GHOSH, A., LABRIOLA, M., BIRIS, A. S., DERVISHI, E., WATANABE, F., WANG, T., SLABOCH, C., OVAERT, T. C. & BISWAS, A. 2013. Fabrication of bionanocomposites comprising flat nanocrystals of calcium in collagen fibers exhibiting hardness comparable to metal. *RSC Advances*, 3, 20315-20323.

BIRCH, R. 2011. *Surgical disorders of the peripheral nerves*.

CASTRO, C., EVORA, C., BARO, M., SORIANO, I. & SANCHEZ, E. 2005. Two-month ciprofloxacin implants for multibacterial bone infections. *European Journal of Pharmaceutics and Biopharmaceutics*, 60, 401-406.

DE RUITER, G. C. W., MALESSY, M. J. A., YASZEMSKI, M. J., WINDEBANK, A. J. & SPINNER, R. J. 2009. Designing ideal conduits for peripheral nerve repair. *Neurosurgical focus*, 26, E5-E5.

GNAVI, S., FORNASARI, B. E., TONDA-TURO, C., LAURANO, R., ZANETTI, M., CIARDELLI, G. & GEUNA, S. 2015. The Effect of Electrospun Gelatin Fibers Alignment on Schwann Cell and Axon Behavior and Organization in the Perspective of Artificial Nerve Design. *International Journal of Molecular Sciences*, 16, 12925-12942.

HENLEY, J. & POO, M.-M. 2004. Guiding Neuronal Growth Cones by Ca(2+) Signals: During axon pathfinding in the developing nervous system, spatiotemporal patterns of Ca(2+) signals can govern growth cone extension and steering—by symmetric versus asymmetric regulation of cytoskeletal and membrane dynamics. *Trends in cell biology*, 14, 320-330.

HSU, S. H., KUO, W. C., CHEN, Y. T., YEN, C. T., CHEN, Y. F., CHEN, K. S., HUANG, W. C. & CHENG, H. 2013. New nerve regeneration strategy combining laminin-coated chitosan conduits and stem cell therapy. *Acta Biomater*, 9, 6606-15.

KEATING, J. F. & MCQUEEN, M. M. 2001. Substitutes for autologous bone graft in orthopaedic trauma. *The Journal of bone and joint surgery. British volume*, 83, 3-8.

LI, Z., RAMAY, H. R., HAUCH, K. D., XIAO, D. & ZHANG, M. 2005. Chitosan-alginate hybrid scaffolds for bone tissue engineering. Biomaterials, 26, 3919-3928.

NIKOOBAKHT, B. & EL-SAYED, M. A. 2003. Preparation and Growth Mechanism of Gold Nanorods (NRs) Using Seed-Mediated Growth Method. *Chemistry of Materials*, 15, 1957-1962.

ORZA, A. I., MIHU C FAU-SORITAU, O., SORITAU O FAU-DIUDEA, M., DIUDEA M FAU-FLOREA, A., FLOREA A FAU-MATEI, H., MATEI H FAU-BALICI, S., BALICI S FAU-MUDALIGE, T., MUDALIGE T FAU-KANARPARDY, G. K., KANARPARDY GK FAU-BIRIS, A. S. & BIRIS, A. S. 2014. Multistructural biomimetic substrates for controlled cellular differentiation. *Nanotechnology*, 25, 1-13.

PAVIOLO, C., HAYCOCK, J. W., CADUSCH, P. J., MCARTHUR, S. L. & STODDART, P. R. 2014. Laser exposure of gold nanorods can induce intracellular calcium transients. *J Biophotonics*, 7, 761-5.

RAMBURRUN, P., KUMAR, P., CHOONARA, Y. E., BIJUKUMAR, D., DU TOIT, L. C. & PILLAY, V. 2014. A Review of Bioactive Release from Nerve Conduits as a Neurotherapeutic Strategy for Neuronal Growth in Peripheral Nerve Injury. *BioMed Research International*, 2014, 19.

ROUSSEAU, M., ANDERSON DE FAU-LILLICH, J. D., LILLICH JD FAU -APLEY, M. D., APLEY MD FAU-JENSEN, P. J., JENSEN PJ FAU-BIRIS, A. S. & BIRIS, A. S. 2014. In vivo assessment of a multicomponent and nanostructural polymeric matrix as a delivery system for antimicrobials and bone morphogenetic protein-2 in a unicortical tibial defect in goats. *American Journal of Veterinary Research*, 75, 240-250.

SCHMIDT, C. E. & LEACH, J. B. 2003. Neural Tissue Engineering: Strategies for Repair and Regeneration. *Annual Review of Biomedical Engineering*, 5, 293-347.

VELLA, F. 1994. Molecular biology of the cell (third edition): By B Alberts, D Bray, J Lewis, M Raff, K Roberts and J D Watson. pp 1361. Garland Publishing, New York and London. 1994. *Biochemical Education*, 22, 164-164.

VOGELIN, E., JONES, N. F., HUANG, J. I., BREKKE, J. H. & LIEBERMAN, J. R. 2005. Healing of a Critical-Sized Defect in the Rat Femur with Use of a Vascularized Periosteal Flap, a Biodegradable Matrix, and Bone Morphogenetic Protein. *The Journal of Bone & Joint Surgery*, 87, 1323-1331.

What is claimed is:

1. A two dimensional (2D) active plasmonic scaffold, comprising:
   a polymer film having a first surface;
   a first nanoparticle layer having first nanoparticles partially embedded on the first surface of the polymer film, wherein the first nanoparticles comprising first functional groups attached thereon; and
   a second nanoparticle layer comprising second nanoparticles disposed on the first nanoparticles, wherein the second nanoparticles comprises second functional groups attached thereon, and the second functional groups are different from the first functional groups,
   wherein the first functional groups are one of —COOH and —NH$_2$, the second functional groups are the other one of —COOH and —NH$_2$, and the first functional groups and the second functional groups are covalently bonded.

2. The 2D active plasmonic scaffold of claim 1, wherein the polymer film is made from chitosan.

3. The 2D active plasmonic scaffold of claim 1, further comprising active molecules attached to at least one of the first functional groups and the second functional groups.

4. The 2D active plasmonic scaffold of claim 1, further comprising active molecules attached to the first functional groups.

5. The 2D active plasmonic scaffold of claim 4, wherein the active molecules comprises at least one of extracellular proteins and drugs.

6. A three dimensional (3D) active plasmonic scaffold, comprising:
   a tubular member; and
   a plurality of strip members, stacked together and disposed inside the tubular member,
   wherein each of the tubular member and the plurality of strip members are made of the 2D active plasmonic scaffold of claim 1; and
   wherein sizes of the strip members match an inner space of the tubular member.

7. The three dimensional (3D) active plasmonic scaffold of claim 6, wherein the tubular member is formed by rolling the 2D active plasmonic scaffold, and the first surface of the 2D active plasmonic scaffold faces inside of the tubular member.

8. The three dimensional (3D) active plasmonic scaffold of claim 6, wherein the tubular member and the strip members are stuck together through welding using acetic acid and stabilizing using sodium hydroxide.

9. A method for making a two dimensional (2D) active plasmonic scaffold, comprising:
   providing a first polymer film and first nanoparticles; and
   embedding the first nanoparticles partially on a first surface of the first polymer film to form a first nanoparticle layer,
   wherein the first nanoparticles comprising first functional groups attached thereon,
   adding, second nanoparticles onto the embedded first nanoparticles to form a second nanoparticle layer, wherein the second nanoparticles having second functional groups attached thereon, and the second functional groups are different from the first functional groups,
   wherein the first functional groups are one of —COOH and —NH$_2$, and the second functional groups are the other one of —COOH and —NH$_2$, and the first functional groups and the second functional groups are covalently bonded.

10. The method of claim 9, wherein the first polymer film is provided by:
    dissolving 2 mg chitosan in 100 ml of 1% acetic acid, and stirring for 24 hours to obtain a uniform polymer solution; and
    casting the uniform polymer solution in a glass mold and drying inside a furnace for 24 hours at 50° C. to obtain the first polymer film.

11. The method of claim 9, wherein the first nanoparticles are gold nanorods with functional groups (AuNR—X), and the AuNR—X are provided by:
    mixing 5 ml of 0.2 M cetyl trimethyl ammonium bromide (CTAB) solution with 5 ml 0.0005 M chloroauric acid (HAuCl$_4$) solution, and then adding 600 ml of 0.01 M sodium borohydrid (NaBH$_4$) solution and mixing to form a seed solution;
    mixing 5 ml of 0.2 M CTAB solution with 150 ml of 0.004 M silver nitrate solution, and then adding 5 ml of 0.001 M HauCl$_4$ and mixing to form a first mixture;
    adding 70 ml of 0.0788 M ascorbic acid to the first mixture to form a second mixture;
    adding 12 ml of the seed solution to the second mixture to form a third mixture;
    maintaining the third mixture at 30° C. for 40 minutes;
    centrifuging the third mixture at 10,000 rpm for 30 minutes to obtain the gold nanorods (AuNRs);
    dispersing the AuNRs in 2 ml of thiolated polyethylene glycol with functional groups (HS-PEG-NH$_2$ or HS-PEG-COOH) and stirring for 15 minutes;
    adding 1.8 ml of thiolated polyethylene glycol (HS-PEG) stabilizer and stirring at room temperature overnight;
    centrifuging at 10,000 rpm for 20 minutes; and
    washing and re-suspending in 1X phosphate buffered saline (PBS) to form the AuNR—X.

12. The method of claim 11, wherein the step of embedding comprises:
    applying 1% acetic acid onto the first surface of the first polymer film;
    adding 2 mg/ml of the AuNR—X in an aqueous solution to the first surface of the first polymer film;
    shaking the first polymer film with the added 1% acetic acid and the AuNR—X; and
    keeping the mold inside a furnace for 24 hours at 50° C. to obtain the 2D active plasmonic scaffold.

13. The method of claim 9, further comprising: adding active molecules onto the second nanoparticles, wherein the active molecules interact with the second functional groups.

14. The method of claim 9, further comprising:
    adding active molecules onto the first nanoparticles, wherein the active molecules interact with the first functional groups.

15. The method of claim 14, wherein the active molecules comprises at least one of extracellular proteins and drugs.

16. A method for making a three dimensional (3D) active plasmonic scaffold, comprising:
    rolling a first active plasmonic scaffold to form a conduit;
    cutting a second active plasmonic scaffold to form strips;
    filling the conduit with the strips;
    wherein each of the conduit member and the plurality of strip members are made of the 2D active plasmonic scaffold of claim 1,
    applying a bonding solution over the conduit and the strips to stick the conduit and the strips to each other;
    immersing the conduit and the strips in a stabilizing solution to stabilize the conduit and the strips; and
    washing the conduit and the strips to obtain the 3D active plasmonic scaffold.

17. The method of claim 16, wherein each of the first active plasmonic scaffold and the second active plasmonic scaffold comprises a polymer layer and a nanoparticle layer partially embedded on one side of the polymer layer.

18. The method of claim 17, wherein the nanoparticle layer comprises gold nanorods with functional groups (AuNR—X) of —$NH_2$ or —COOH.

19. The method of claim 16, wherein the binding solution 1% acetic acid, and the stabilizing solution is sodium hydroxide.

* * * * *